United States Patent
Gaddam et al.

(10) Patent No.: US 10,226,636 B2
(45) Date of Patent: Mar. 12, 2019

(54) MANAGING RECHARGE POWER FOR IMPLANTABLE MEDICAL DEVICES

(71) Applicant: Medtronic, Inc., Minneapolis, MN (US)

(72) Inventors: Venkat R. Gaddam, Plymouth, MN (US); Reid K. Bornhoft, Lino Lakes, MN (US); David P. Olson, Minnetrista, MN (US); Prabhakar A. Tamirisa, Brooklyn Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 15/560,950

(22) PCT Filed: Apr. 22, 2016

(86) PCT No.: PCT/US2016/028917
§ 371 (c)(1),
(2) Date: Sep. 22, 2017

(87) PCT Pub. No.: WO2016/172530
PCT Pub. Date: Oct. 27, 2016

(65) Prior Publication Data
US 2018/0043167 A1    Feb. 15, 2018

Related U.S. Application Data

(60) Provisional application No. 62/152,617, filed on Apr. 24, 2015.

(51) Int. Cl.
*H02J 7/02*    (2016.01)
*A61N 1/378*    (2006.01)
*H02J 7/04*    (2006.01)

(52) U.S. Cl.
CPC ............ *A61N 1/3787* (2013.01); *H02J 7/025* (2013.01); *H02J 7/027* (2013.01); *H02J 7/047* (2013.01)

(58) Field of Classification Search
CPC .................................. H02J 7/027; H02J 7/047
(Continued)

(56) References Cited

U.S. PATENT DOCUMENTS 8,040,110 B2   10/2011   Al-anbuky et al.
8,326,426 B2   12/2012   Thornton et al.
(Continued)

FOREIGN PATENT DOCUMENTS

WO   2009055579 A1   4/2009
WO   2009134467 A1   11/2009

OTHER PUBLICATIONS

Lazzi, "Thermal Effects of Bioimplants," Power Dissipation Characteristics and Computational Methods, IEEE Engineering in Medicine and Biology Magazine, Sep./Oct. 2005, 7 pp.
(Continued)

*Primary Examiner* — Edward Tso
*Assistant Examiner* — Aaron Piggush
(74) *Attorney, Agent, or Firm* — Shumaker & Sieffert, P.A.

(57) ABSTRACT

Devices, systems, and techniques for estimating energy transfer to tissue of a patient during battery charging for an implantable medical device are disclosed. Implantable medical devices may include a rechargeable power source that can be transcutaneously charged. An external charging device may calculate an estimated energy transfer to tissue of the patient that may include a resistive heat loss from the rechargeable power source and/or electromagnetic energy transfer directly to tissue. Based on the estimated energy transfer, the external charging device may select a power
(Continued)

level for charging of the rechargeable power source. In one example, the charging device may select a high power level when the estimated energy transfer has not exceeded an energy transfer threshold and select a low power level when the estimated energy transfer has exceeded the energy transfer threshold.

23 Claims, 9 Drawing Sheets

(58) Field of Classification Search
USPC .......................... 320/108, 134, 150; 607/61
See application file for complete search history.

(56) References Cited

U.S. PATENT DOCUMENTS

| | | |
|---|---|---|
| 8,509,912 B2 | 8/2013 | Morgan et al. |
| 2004/0098068 A1 | 5/2004 | Carbunaru et al. |
| 2009/0276014 A1* | 11/2009 | Morgan ............... A61N 1/3787 607/61 |
| 2010/0010582 A1 | 1/2010 | Carbunaru et al. |
| 2011/0087307 A1* | 4/2011 | Carbunaru ........... A61N 1/3605 607/61 |
| 2012/0262108 A1 | 10/2012 | Olson et al. |
| 2013/0197613 A1 | 8/2013 | Kelly et al. |
| 2013/0193914 A1 | 9/2013 | Gaddam et al. |

OTHER PUBLICATIONS

"IEEE Standard for Safety Levels with Respect to Human Exposure to Electromagnetic Fields, 0-3 kHz," IEEE Standard C95.6™—2002, Oct. 23, 2002, 50 pp.

"IEEE Standard for Safety Levels with Respect to Human Exposure Radio Frequency Electromagnetic Fields, 3 kHz to 300 GHz," IEEE Standard C95.1™—2005, Apr. 19, 2006, 250 pp. [uploaded in parts].

International Search Report and Written Opinion from International Application No. PCT/US2016/028917, dated Jul. 25, 2016, 11 pp.

International Preliminary Report on Patentability from International Application No. PCT/US2016/028917, dated Nov. 2, 2017, 8 pp.

* cited by examiner

MANAGING RECHARGE POWER FOR IMPLANTABLE MEDICAL DEVICES

This application is a National Stage application under 35 U.S.C. § 371 of PCT Application No. PCT/US2016/028917, entitled "MANAGING RECHARGE POWER FOR IMPLANTABLE MEDICAL DEVICES" and filed on Apr. 22, 2016, which claims the benefit of U.S. Provisional Patent Application No. 62/152,617, entitled "MANAGING RECHARGE POWER FOR IMPLANTABLE MEDICAL DEVICES" and filed on Apr. 24, 2015. The entire contents of application nos. PCT/US2016/028917 and 62/152,617 are incorporated herein by reference.

TECHNICAL FIELD

The disclosure relates to implantable medical devices and, more particularly, systems and methods for recharging power supplies of implantable medical devices.

BACKGROUND

Implantable medical devices may be used to monitor a patient condition and/or deliver therapy to the patient. In long term or chronic uses, implantable medical devices may include a rechargeable power source (e.g., comprising one or more capacitors or batteries) that extends the operational life of the medical device to weeks, months, or even years over a non-rechargeable device.

When the energy stored in the rechargeable power source has been depleted, the patient may use an external charging device to recharge the power source. Since the rechargeable power source is implanted in the patient and the charging device is external of the patient, this charging process may be referred to as transcutaneous charging. In some examples, transcutaneous charging may be performed via inductive coupling between a primary coil in the charging device and a secondary coil in the implantable medical device. When a current is applied to the primary coil and the primary coil is aligned to the secondary coil, electrical current is induced in the secondary coil within the patient. Therefore, the external charging device does not need to physically connect with the rechargeable power source for charging to occur.

SUMMARY

In general, the disclosure is directed to devices, systems, and techniques for estimating energy transferred to tissue of a patient during a battery charging period for an implantable medical device (IMD). An external charging device may be used to transcutaneously charge a rechargeable power source of the IMD. The external charging device may calculate an estimated energy transferred to tissue of the patient during the charging process. Based on the estimated energy transfer calculation, the external charging device may control the delivery of charging power to the rechargeable power source. For example, the external charging device may select a power level for subsequent charging of the rechargeable power source based on the estimated energy already transferred to the patient.

In one aspect, the disclosure is directed to a method for controlling charging of a rechargeable power source of an implantable medical device in a patient. The method includes determining, by a processor, an estimated power stored in the rechargeable power source during charging of the rechargeable power source, the estimated power stored being separate from a resistive heat loss of the rechargeable power source during charging of the rechargeable power source, calculating, by the processor, an estimated energy transfer to tissue of the patient during charging of the rechargeable power source, the estimated energy transfer including the resistive heat loss of the rechargeable power source, and controlling, by the processor and based on the estimated energy transfer to the tissue, energy generation by a primary coil of an external charging device for charging the rechargeable power source via a secondary coil of the implantable medical device.

In another aspect, the disclosure is directed to a device that includes a processor configured to determine an estimated power stored in a rechargeable power source of an implantable medical device in a patient during charging of the rechargeable power source, the estimated power stored being separate from a resistive heat loss of the rechargeable power source during charging of the rechargeable power source, calculate an estimated energy transfer to tissue of the patient during charging of the rechargeable power source, the estimated energy transfer including the resistive heat loss of the rechargeable power source, and control, based on the estimated energy transfer to the tissue, energy generation by a primary coil of an external charging device for charging the rechargeable power source via a secondary coil of the implantable medical device.

In a further aspect, the disclosure is directed to a system that includes means for determining an estimated power stored in the rechargeable power source during charging of the rechargeable power source, the estimated power stored being separate from a resistive heat loss of the rechargeable power source during charging of the rechargeable power source, means for calculating an estimated energy transfer to tissue of the patient during charging of the rechargeable power source, the estimated energy transfer including the resistive heat loss of the rechargeable power source, and means for controlling, based on the estimated energy transfer to the tissue, energy generation by a primary coil of an external charging device for charging the rechargeable power source via a secondary coil of the implantable medical device.

DETAILED DESCRIPTION

Figure 1:
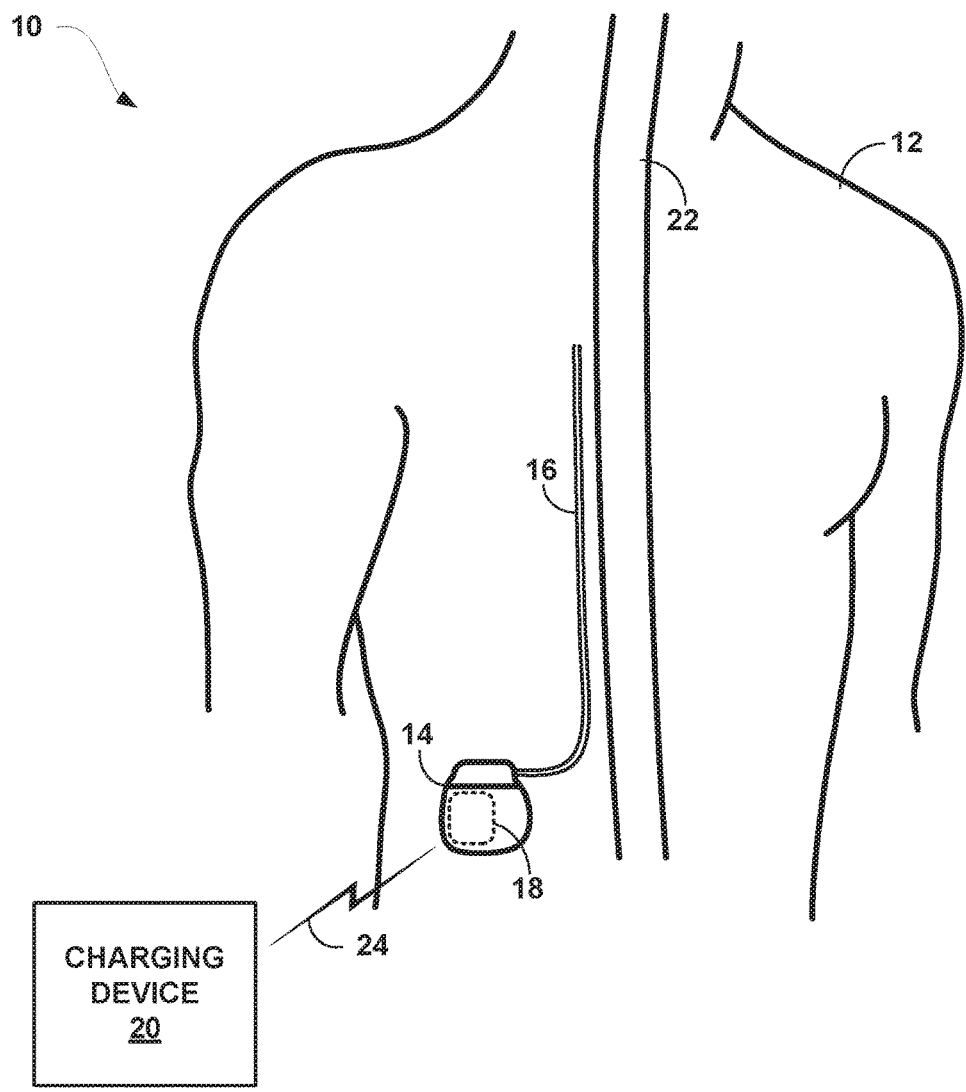
FIG. 1 is a conceptual diagram illustrating an example system that includes an implantable medical device (IMD) and an external charging device that charges a rechargeable power source of the IMD.

This disclosure is generally directed to devices, systems, and techniques for estimating energy transfer delivered to tissue of a patient and, in some examples, controlling energy generation by a primary coil to charge a rechargeable power source based on the estimated energy transfer. Implantable medical devices (IMDs) may be implanted within a patient and used to monitor a parameter of the patient and/or deliver a therapy to the patient. To extend the operational life of the IMD, the IMD may include a rechargeable power source (e.g., one or more capacitors and/or batteries). When the rechargeable power source is being recharged, the power transmitted to the IMD may generate heat that increases the temperature of the IMD. In order to prevent this increased temperature from damaging patient tissue adjacent to the IMD or causing discomfort to the patient, charging sessions may be limited to predetermined durations and/or reduced power levels may be used to recharge the rechargeable power source. However, this approach may increase recharge durations and/or prevent the rechargeable power source from being fully charged.

As disclosed herein, an estimate of the energy transferred (e.g., an estimated energy transfer) to tissue of the patient during recharging may be calculated periodically or on a continual basis. The estimated energy transfer may take into account several causes of energy exposure to the tissue of the patient. For example, the estimated energy transfer may include heat generated by a secondary coil within the IMD, heat generated by internal circuits within the IMD, heat generated (or heat losses) due to the resistance of the rechargeable power source (e.g., the IMD battery), and/or energy directly transferred to or absorbed by patient tissue due to direct exposure to electromagnetic energy generated by the primary coil of the charging device.

The heat losses due to the resistance of the rechargeable power source may be negligible for larger IMDs and larger batteries. However, as IMDs become increasingly miniaturized, their respective batteries generally decrease in size and increase in resistance. Therefore, accounting for resistive heat losses in an IMD battery may provide more accurate estimation of energy transfer to tissue when charging the batteries of smaller IMDs. In addition, energy absorbed directly by tissue from a primary charging coil may be negligible for relatively low radiofrequencies (e.g., frequencies lower than 100 KHz). However, as the radiofrequencies are increased in order to transfer energy to smaller secondary coils of smaller IMDs, this higher frequency electromagnetic radiation may induce tissue heating. Therefore, accounting for direct electromagnetic energy absorption by tissue may provide more accurate estimation of energy transfer to tissue when transferring energy to coils of smaller IMDs.

The external charging device may monitor the estimated energy transfer and control the charging power level of the charging process to limit the heat generated in and around the IMD. For example, the charging device may select a high power level to charge the rechargeable power source at a high rate until the calculated estimated energy transfer indicates the power level needs to be reduced. The charging device may then terminate charging or select a lower power level to continue charging the rechargeable power source at lower IMD temperatures.

The estimated energy transfer feedback may thus reduce the need to conservatively estimate recharge times and recharge power levels to keep the temperature of the IMD within safe limits. Instead, the charging device may charge the rechargeable power source at high rates until the estimated energy transfer indicates that the charge power level needs to be reduced. Lower power levels may be used to continue charging the rechargeable power source until the power source is fully charged. This closed loop feedback approach may reduce the amount of time needed to charge rechargeable power sources and/or increase the likelihood that the rechargeable power source is fully charged after a recharge session because energy transfer to tissue of the patient is monitored instead of relying on conservative "worst-case scenarios" that can result in premature termination of a recharge session.

The estimated energy transfer may be an indication, or estimation, of the total amount of energy (e.g., heat, etc.) to which tissue surrounding the IMD has been exposed. Even at temperatures too low to cause immediate tissue necrosis, elevated temperatures from energy transferred to tissue of the patient may still be undesirable for the patient. Therefore, it may be useful to estimate and monitor the amount of time that tissue is exposed to elevated energy transfers (e.g., power between 50-150 milliwatts (mW), 50-600 mW, and/or 50-2000 mW). This estimated energy transfer may be used to control the recharge process and prevent uncomfortable and undesirable elevated temperatures. For example, the estimated energy transfer from the IMD to the tissue of a patient may be calculated by subtracting the heat loss in the primary coil and the estimated power stored in the rechargeable power source from the power delivered to the primary circuit of the external charging device. The remaining power may be an estimation of the energy (i.e., heat) lost from the system to the surrounding tissue of the patient. Since the exact energy transferred to the patient may be difficult to precisely measure, the estimated energy transfer described herein may be used as an estimation of the actual energy transfer delivered to the patient. However, the calculated estimated energy transfer described herein may be substantially similar to the actual energy transfer received by the patient. The power level used to charge the rechargeable power source may then be selected based on the comparison of the estimated energy transfer to one or more thresholds.

In some examples, the charging device may select power levels with decreasing intensity as the estimated energy transfer reaches a threshold. Incrementally decreasing the power level may minimize the risk of exceeding the estimated energy transfer threshold from residual heat in the IMD even after reducing the power level.

FIG. 1 is a conceptual diagram illustrating an example system 10 that includes an implantable medical device (IMD) 14 and an external charging device 20 that charges a rechargeable power source 18. Although the techniques described in this disclosure are generally applicable to a variety of medical devices including medical devices such as patient monitors, electrical stimulators, or drug delivery devices, application of such techniques to implantable neurostimualtors will be described for purposes of illustration. More particularly, the disclosure will refer to an implantable neurostimulation system for use in spinal cord stimulation therapy, but without limitation as to other types of medical devices.

As shown in FIG. 1, system 10 includes an IMD 14 and external charging device 20 shown in conjunction with a patient 12, who is ordinarily a human patient. In the example of FIG. 1, IMD 14 is an implantable electrical stimulator that delivers neurostimulation therapy to patient 12, e.g., for relief of chronic pain or other symptoms. Generally IMD 14 may be a chronic electrical stimulator that remains implanted within patient 12 for weeks, months, or even years. In the example of FIG. 1, IMD 14 and lead 16 may be directed to delivering spinal cord stimulation therapy. In other examples, IMD 14 may be a temporary, or trial, stimulator used to screen or evaluate the efficacy of electrical stimulation for chronic therapy. IMD 14 may be implanted in a subcutaneous tissue pocket, within one or more layers of muscle, or other internal location. IMD 14 includes rechargeable power source 18 and IMD 14 is coupled to lead 16.

Electrical stimulation energy, which may be constant current or constant voltage based pulses, for example, is delivered from IMD 14 to one or more targeted locations within patient 12 via one or more electrodes (not shown) of lead 16. The parameters for a program that controls delivery of stimulation energy by IMD 14 may include information identifying which electrodes have been selected for delivery of stimulation according to a stimulation program, the polarities of the selected electrodes, i.e., the electrode configuration for the program, and voltage or current amplitude, pulse rate, pulse shape, and pulse width of stimulation delivered by the electrodes. Electrical stimulation may be delivered in the form of stimulation pulses or continuous waveforms, for example.

In the example of FIG. 1, lead 16 is disposed within patient 12, e.g., implanted within patient 12. Lead 16 tunnels through tissue of patient 12 from along spinal cord 22 to a subcutaneous tissue pocket or other internal location where IMD 14 is disposed. Although lead 16 may be a single lead, lead 16 may include a lead extension or other segments that may aid in implantation or positioning of lead 16. In addition, a proximal end of lead 16 may include a connector (not shown) that electrically couples to a header of IMD 14. Although only one lead 16 is shown in FIG. 1, system 10 may include two or more leads, each coupled to IMD 14 and directed to similar or different target tissue sites. For example, multiple leads may be disposed along spinal cord 22 or leads may be directed to spinal cord 22 and/or other locations within patient 12.

Lead 16 may carry one or more electrodes that are placed adjacent to the target tissue, e.g., spinal cord 22 for spinal cord stimulation (SCS) therapy. One or more electrodes may be disposed at a distal tip of lead 16 and/or at other positions at intermediate points along lead 16, for example. Electrodes of lead 16 transfer electrical stimulation generated by an electrical stimulation generator in IMD 14 to tissue of patient 12. The electrodes may be electrode pads on a paddle lead, circular (e.g., ring) electrodes surrounding the body of the lead, conformable electrodes, cuff electrodes, segmented electrodes, or any other type of electrodes capable of forming unipolar, bipolar or multipolar electrode configurations for therapy. In general, ring electrodes arranged at different axial positions at the distal ends of lead 16 will be described for purposes of illustration.

In alternative examples, lead 16 may be configured to deliver stimulation energy generated by IMD 14 to stimulate one or more sacral nerves of patient 12, e.g., sacral nerve stimulation (SNS). SNS may be used to treat patients suffering from any number of pelvic floor disorders such as pain, urinary incontinence, fecal incontinence, sexual dysfunction, or other disorders treatable by targeting one or more sacral nerves. Lead 16 and IMD 14 may also be configured to provide other types of electrical stimulation or drug therapy (e.g., with lead 16 configured as a catheter). For example, lead 16 may be configured to provide deep brain stimulation (DBS), peripheral nerve stimulation (PNS), or other deep tissue or superficial types of electrical stimulation. In other examples, lead 16 may provide one or more sensors configured to allow IMD 14 to monitor one or more parameters of patient 12. The one or more sensors may be provided in addition to, or in place of, therapy delivery by lead 16.

IMD 14 delivers electrical stimulation therapy to patient 12 via selected combinations of electrodes carried by lead 16. The target tissue for the electrical stimulation therapy may be any tissue affected by electrical stimulation energy, which may be in the form of electrical stimulation pulses or waveforms. In some examples, the target tissue includes nerves, smooth muscle, and skeletal muscle. In the example illustrated by FIG. 1, the target tissue for electrical stimulation delivered via lead 16 is tissue proximate spinal cord 22 (e.g., one or more target locations of the dorsal columns or one or more dorsal roots that branch from spinal cord 22. Lead 16 may be introduced into spinal cord 22 via any suitable region, such as the thoracic, cervical or lumbar regions. Stimulation of dorsal columns, dorsal roots, and/or peripheral nerves may, for example, prevent pain signals from traveling through spinal cord 22 and to the brain of the patient. Patient 12 may perceive the interruption of pain signals as a reduction in pain and, therefore, efficacious therapy results. For treatment of other disorders, lead 16 may be introduced at any exterior location of patient 12. In this manner, skin opening 18 may be located at any exterior skin location in other examples.

Although lead 16 is described as generally delivering or transmitting electrical stimulation signals, lead 16 may additionally or alternatively transmit electrical signals from patient 12 to IMD 14 for monitoring. For example, IMD 14 may utilize detected nerve impulses to diagnose the condition of patient 12 or adjust the delivered stimulation therapy. Lead 16 may thus transmit electrical signals to and from patient 12.

A user, such as a clinician or patient 12, may interact with a user interface of an external programmer (not shown) to program IMD 14. Programming of IMD 14 may refer generally to the generation and transfer of commands, programs, or other information to control the operation of IMD 14. For example, the external programmer may transmit programs, parameter adjustments, program selections, group selections, or other information to control the operation of IMD 14, e.g., by wireless telemetry or wired connection.

In some cases, an external programmer may be characterized as a physician or clinician programmer if it is primarily intended for use by a physician or clinician. In other cases, the external programmer may be characterized as a patient programmer if it is primarily intended for use by a patient. A patient programmer is generally accessible to patient 12 and, in many cases, may be a portable device that may accompany the patient throughout the patient's daily routine. In general, a physician or clinician programmer may support selection and generation of programs by a clinician for use by stimulator 14, whereas a patient programmer may support adjustment and selection of such programs by a patient during ordinary use. In other examples, external charging device 20 may be included, or part of, an external programmer. In this manner, a user may program and charge IMD 14 using one device, or multiple devices.

IMD 14 may be constructed of any polymer, metal, or composite material sufficient to house the components of IMD 14 (e.g., components illustrated in FIG. 2) within patient 12. In this example, IMD 14 may be constructed with a biocompatible housing, such as titanium or stainless steel, or a polymeric material such as silicone or polyurethane, and surgically implanted at a site in patient 12 near the pelvis, abdomen, or buttocks. The housing of IMD 14 may be configured to provide a hermetic seal for components, such as rechargeable power source 18. In addition, the housing of IMD 14 may be selected of a material that facilitates receiving energy to charge rechargeable power source 18.

As described herein, rechargeable power source 18 may be included within IMD 14. However, in other examples, rechargeable power source 18 could be located external to a housing of IMD 14, separately protected from fluids of patient 12, and electrically coupled to electrical components of IMD 14. This type of configuration of IMD 14 and rechargeable power source 18 may provide implant location flexibility when anatomical space for implantable devices is minimal. In any case, rechargeable power source 18 may provide operational electrical power to one or more components of IMD 14.

Rechargeable power source 18 may include one or more capacitors, batteries, or components (e.g. chemical or electrical energy storage devices). Example batteries may include lithium-based batteries, nickel metal-hydride batteries, or other materials. Rechargeable power source 18 is also rechargeable. In other words, rechargeable power source 18 may be replenished, refilled, or otherwise capable of increasing the amount of energy stored after energy has been depleted. Rechargeable power source 18 may be subjected to numerous discharge and recharge cycles (e.g., hundreds or even thousands of cycles) over the life of rechargeable power source 18 in IMD 14. Rechargeable power source 18 may be recharged when fully depleted or partially depleted.

Charging device 20 may be used to recharge rechargeable power source 18 and IMD 14 when implanted in patient 12. Charging device 20 may be a hand-held device, a portable device, or a stationary charging system. In any case, charging device 20 may include components necessary to charge rechargeable power source 18 through tissue of patient 12. In some examples, charging device 20 may only perform charging of rechargeable power source 18. In other examples, charging device 20 may be an external programmer or other devices configured to perform additional functions. For example, when embodied as an external programmer, charging device 20 may transmit programming commands to IMD 14 in addition to charge rechargeable power source 18. In another example, charging device 20 may communicate with IMD 14 to transmit and/or receive information related to the charging of rechargeable power source 18. For example, IMD 14 may transmit temperature information of IMD 14 and/or rechargeable power source 18, received power during charging, the charge level of rechargeable power source 18, charge depletion rates during use, or any other information related to power consumption and recharging of IMD 14 and rechargeable power source 18.

Charging device 20 and IMD 14 may utilize any wireless power transfer techniques that are capable of recharging rechargeable power source 18 of IMD 14 when IMD 14 is implanted within patient 14. In one example, system 10 may utilize inductive coupling between a coil of charging device 20 and a coil of IMD 14 coupled to rechargeable power source 18. In inductive coupling, charging device 20 is placed near implanted IMD 14 such that a primary coil of charging device 20 is aligned with, i.e., placed over, a secondary coil of IMD 14. Charging device 20 may then generate an electrical current in the primary coil based on a selected power level for charging rechargeable power source 18. As described further below, the power level may be selected to control the estimated energy transfer to tissue of patient 12 and/or the charge rate of rechargeable power source 18. When the primary and secondary coils are aligned, the electrical current in the primary coil may magnetically induce an electrical current in the secondary coil within IMD 14. The primary coil may generate electromagnetic energy (e.g., radiofrequency (RF) energy) that is received by the secondary coil. Since the secondary coil is associated with and electrically coupled to rechargeable power source 18, the induced electrical current may be used to increase the loaded voltage, or charge level, of rechargeable power source 18. Although inductive coupling is generally described herein, any type of wireless energy transfer may be used to charge rechargeable power source 18.

During the energy transfer process that charges rechargeable power source 18, some of the energy may be converted into heat at rechargeable power source 18 and/or other components of IMD 14, such as the secondary coil or other charging circuitry. When increased energy levels are used to charge rechargeable power source 18 at a higher rate, the energy transfer (e.g., heat and/or electromagnetic radiation) to tissue of patient 12 may also increase. Although the energy transfer of the IMD 14 housing may not achieve a temperature sufficient to burn or necrose tissue adjacent to the housing of IMD 14, elevated energy transfer to tissue of patient 12 may be undesirable and uncomfortable over time. In addition, higher temperatures may adversely affect the functioning of cells in the tissue. Therefore, charging device 20 may control the power levels used to charge rechargeable power source 18 to reduce or minimize any undesirable energy transfer that could be caused by charging rechargeable power source 18. In some examples, monitoring the energy transfer to tissue, which may include monitoring energy losses and/or the temperature of IMD 14 and/or the temperature of tissue adjacent to the housing of IMD 14, may allow system 10 to minimize patient discomfort during the charging process.

In one example, the power level used by charging device 20 to recharge rechargeable power source 18 may be selected or controlled based on an estimated energy transfer to tissue of tissue of patient 12. The estimated energy transfer may be a metric used to quantify or estimate the total energy transferred to tissue adjacent to IMD 14. In one example, the estimated energy transfer transferred to tissue of the patient from the IMD may be calculated by subtracting the heat loss in the primary coil and the estimated power transferred to, or stored in, the battery from the power delivered to the primary circuit. The resulting estimated energy transfer may be used to equate the delivered power from an external charging device to the tissue to a certain energy level or tissue temperature level. For example, the clinician may want to limit tissue exposure to a predetermined energy threshold or limit (e.g., power at or above a predetermined limit in mW). However, the energy transferred to tissue of patient 12 will likely vary over the charging period. Calculation of the estimated energy transfer may thus allow charging device 20, or IMD 14, to determine when the desired limit to energy transferred (e.g., heat exposure) is reached even if the actual energy transfer varies over time. These calculations of the estimated energy transfer may include resistive heat losses from the rechargeable power source 18 of IMD 14 transferred to tissue from the IMD. When charging, current sent to rechargeable power source 18 may charge the power source and increase the temperature of the power source due to internal resistances of the power source (e.g., a rechargeable battery). In some examples, the estimated energy transfer may also include an estimated energy absorbed by tissue during the recharging process. A portion of the electromagnetic energy generated by the primary coil of charging device 20 may be directly absorbed by tissue exposed to the electromagnetic energy such that the exposed tissue increases in temperature. In any example, the estimated energy transfer may be used to determine the total amount of energy transferred or the extent of energy transferred (e.g., an elevated temperature exposure) for tissue surrounding and/or adjacent to IMD 14.

In some examples, an energy balance approach may be used to calculate the estimated energy transfer according to several different techniques. Each technique may result in an estimated energy transfer that estimates the actual energy transfer received by tissue of patient 12. However, the estimated energy transfer calculated by charging device 20 and/or IMD 14 in system 10 may be substantially similar to the actual energy transfer received by tissue of patient 12. As discussed herein, in some examples, the estimated energy transfer to tissue of patient 12 may be the estimated energy transfer from IMD 14 to tissue of patient 12. This energy transfer from IMD 14 may generally include heat radiating from components of IMD 14 that are also increasing in temperature. However, as discussed in some examples herein, the estimated energy transfer to tissue of patient 12 may include the energy directly absorbed by tissue of patient 12 from charging device 20 instead of, or in addition to, the estimated energy transfer from IMD 14 to tissue of patient 12. By accounting for the resistive heat loss from power source 18 and/or the energy absorbed by tissue of patient 12, the estimated energy transfer calculated by charging device 20 and/or IMD 14 in system 10 may provide an accurate estimate of the actual energy transfer received by tissue of patient 12.

In one example, the energy transferred to tissue of patient 12 may be indirectly calculated, or estimated, based on the total power delivered to the primary coil of charging device 20. For example, the estimated energy transfer may be determined by subtracting the electrical heat loss in the primary coil and the power estimated to have been stored in (or the effective power delivered to) power source 18 (e.g., the energy that was transferred into increased charge of the power source) from the total power delivered to the primary coil, or some combination therein. The remaining power may be indicative of the actual energy transferred to tissue. In this manner, charging device 20 and/or IMD 14 may determine the estimated energy transfer to tissue of patient 12, which may also be the estimated energy transfer from IMD 14 to tissue of patient 12. For example, IMD 14 may measure the actual electrical current induced in the secondary coil and coupled to rechargeable power source 18, and may use an open-circuit voltage of rechargeable power source 18 (in contrast to a measured voltage across the power source). The open-circuit voltage may be determined using a look-up table, equation, or measurements as described herein. The open-circuit voltage may be used to estimate the power that would actually be stored in the power source from electrical current used to increase the charge of power source 18. By using the open-circuit voltage of power source 18 instead of the loaded voltage on power source 18, the resistive heat losses in power source 18 may remain in the calculated energy transferred to tissue instead of being subtracted from the total power to the primary coil. Based on the measured current (e.g., the charge current) and the open-circuit voltage, a processor of IMD 14 may calculate an estimated power stored in rechargeable power source 18. IMD 14 may then transmit the estimated power stored to power source 18 back to charging device 20. Charging device 20 may monitor the generated current in the primary coil and the total power delivered to the primary coil of charging device 20. A processor of charging device 20 may then determine the estimated energy transfer to tissue of patient 12 by subtracting the estimated power stored to power source 18 and the electrical heat loss in the primary coil of charging device 20 from the total power delivered to the primary coil of charging device 20.

System 10 may determine the capacity of rechargeable power source 18, and determine, based on the measured current and determined capacity, the state-of-charge (SOC) of rechargeable power source 18. Based on data of a circuit model of power source 18 in a lookup table, a processor of IMD 14 may determine the open-circuit voltage (i.e., the voltage of power source 18 without a load) of rechargeable power source 18 at the determined SOC of power source 18. In this manner, the open-circuit voltage may be estimated based on factors such as battery age and SOC. Based on the measured current and the open-circuit voltage, a processor of IMD 14 may determine the power stored in (or effective power delivered to) rechargeable power source 18 and the resistive heat loss from power source 18. The effective power delivered to power source 18 for increasing battery charge may incorporate the resistive heat loss from power source 18 when subtracting the effective power delivered from the power delivered to the primary coil. In other words, the resistive heat losses that may be transferred to tissue are not included as energy stored in rechargeable power source 18. IMD 14 may then transmit the determined effective power delivered to power source 18 back to charging device 20.

In this manner, the energy transferred to tissue of patient 12 may be indirectly calculated, or estimated, based on the total power delivered to the primary coil of charging device 20 and the resistive heat loss from power source 18. The resistive heat loss from power source 18 may be the heat generated within power source 18 from electrical current applied to the internal resistance of power source 18. The heat caused by the internal resistance may be radiated out from IMD 14 and transferred to the surrounding tissue of patient 12. In another example, the estimated energy transfer may be determined by subtracting the electrical heat loss in the primary coil and the total power delivered to power source 18 from the total power delivered to the primary coil and adding the resistive heat loss from power source 18, or some combination therein. In this manner, charging device 20 and/or IMD 14 may determine the estimated energy transfer to tissue of patient 12, which may include the estimated energy transfer from IMD 14 to tissue of patient 12. For example, IMD 14 may measure the actual electrical current (e.g., the charge current) induced in the secondary coil and applied to rechargeable power source 18, measure the loaded voltage across power source 18, and multiply the charge current by the loaded voltage to calculate the power delivered to power source 18. In addition, the resistive heat loss from power source 18 may be determined by multiplying the square of the charge current by the resistance of the power source 18. The resistive heat loss may then be added to the remainder of the total power delivered to the primary coil after subtracting the heat loss at the primary coil and the total power delivered to power source 18.

In some examples, where the resistive heat loss from power source 18 may be negligible, such as large battery circuits, a processor of charging device 20 may then determine the estimated energy transfer to tissue of patient 12 by subtracting the effective power delivered to power source 18 and the electrical heat loss in the primary coil of charging device 20 from the total power delivered to the primary coil of charging device 20. However, in other examples where the resistive heat loss from power source 18 may not be negligible (e.g., small batteries or other batteries having higher internal resistances), a processor of charging device 20 may determine the estimated energy transfer to tissue of patient 12 by subtracting the estimated power stored in power source 18 and the electrical heat loss in the primary coil of charging device 20 from the total power delivered to the primary coil of charging device 20. This process may effectively incorporate resistive heat losses from power source 18 into the energy transferred to tissue during a charging session. Alternatively, the processor may calculate and add the resistive heat loss of power source 18 to other energy transferred to tissue in order to include the resistive heat loss of power source 18.

In addition, or alternatively, the energy transferred to tissue of patient 12 may be indirectly calculated, or estimated, based on the total power delivered to the primary coil of charging device 20 and the energy absorbed by tissue of patient 12 between the primary coil of charging device 20 and the secondary coil of IMD 14. For example, the estimated energy transfer may be determined by subtracting the electrical heat loss in the primary coil and the estimated power stored in power source 18 from the total power delivered to the primary coil, and adding the energy absorbed in tissue of patient 12 to the total power delivered to the primary coil, or some combination therein. In this manner, charging device 20 and/or IMD 14 may determine the estimated energy transfer to tissue of patient 12, which may include the estimated energy transfer to tissue of patient 12 from IMD 14. For example, IMD 14 may measure the actual electrical current (e.g., the charge current) induced in the secondary coil coupled to rechargeable power source 18, determine the open-circuit voltage of rechargeable power source 18, and determine the operating frequency of the secondary coil of IMD 14. Based on the measured current, the open-circuit voltage, and an energy absorption model of tissue of patient 12 at the determined operating frequency, a processor of IMD 14 may determine the energy absorbed by tissue of patient 12 during a charging session. For example, based on the measured current and the open-circuit voltage of power source 18, a processor of IMD 14 and/or charging device 20 may determine the power stored in rechargeable power source 18 by multiplying the measured current and the open-circuit voltage. Based on data of specific absorption rate at the determined frequency from a lookup table stored in memory, a processor of IMD 14 and/or charging device 20 may determine the energy absorbed by tissue of patient 12 from the electromagnetic energy generated by the primary coil of charging device 20. IMD 14 may then transmit the determined power stored in power source 18 and the determined energy absorbed by tissue of patient 12 back to charging device 20. Charging device 20 may use this information to monitor energy transfer to tissue and/or control charging of charging device 20.

In some examples, where the energy absorbed by tissue of patient 12 may be negligible at the operating frequency of charging device 20 and IMD 14, a processor of charging device 20 may then determine the estimated energy transfer to tissue of patient 12 by subtracting the total power delivered to power source 18 and the electrical heat loss in the primary coil of charging device 20 from the total power delivered to the primary coil of charging device 20. In other examples, where the energy absorbed by tissue of patient 12 may not be negligible at the operating frequency of charging device 20 and IMD 14, a processor of charging device 20 may determine the estimated energy transfer to tissue of patient 12 by subtracting the power delivered to power source 18 and the electrical heat loss in the primary coil of charging device 20 from the total power delivered to the primary coil of charging device 20, and adding the energy absorbed by tissue of patient 12.

In another example, the energy transferred to tissue of patient 12 may be indirectly calculated, or estimated, to include both the resistive heat loss from power source 18 and the energy directly absorbed by tissue of patient 12 from the primary coil of charging device 20. For example, the estimated energy transfer may be determined by subtracting the electrical heat loss in the primary coil and the estimated power stored in power source 18 from the total power delivered to the primary coil, and then adding energy absorbed in tissue of patient 12 from the primary coil.

In some examples, the measured or estimated energy transfer to tissue of patient 12 may be applied to a tissue model to calculate the expected tissue temperature. Tissue model may be one or more equations that incorporate one or more of the energy capacity and/or absorption of tissue adjacent IMD 14, density of surrounding tissue, inherent body temperature, surface area of the housing of IMD 14, estimated surface area of tissue surrounding IMD 14, depth of IMD 14 from the skin of patient 12, orientation of the secondary coil within patient 12, or any other variable that would affect the temperature of tissue surrounding and/or in immediate contact with the housing of IMD 14. The tissue model may even be modified over time to account for tissue ingrowth, scar tissue, encapsulation, and other tissue changes due to the biological interaction between the housing of IMD 14 and patient 12. The estimated energy transfer may be inputted into tissue model to calculate an estimation of tissue temperature as charging device 20 recharges rechargeable power source 18.

Using the estimated energy transfer techniques, tissue temperature may be calculated by processors of charging device 20, IMD 14, or some combination thereof. For example, charging device 20 may unilaterally calculate tissue temperature using tissue model and the estimated energy transfer. In another example, one or more measured variables may be communicated from IMD 14 to charging device 20 such that charging device can calculate tissue temperature. IMD 14 may transmit detected alignment of the primary and secondary coils and/or the electrical current induced in the secondary coil. In an alternative embodiment, IMD 14 may determine the estimated energy transfer and calculate tissue temperature based on that determined energy transfer. IMD 14 may then transmit the calculated tissue temperature to charging device 20, calculate and transmit the estimated energy transfer to charging device 20 based on tissue temperature, or even transmit a selected power level for charging device 20 based on the calculated estimated energy transfer. According to these examples, the processes needed to determine a tissue temperature (e.g., using a measured temperature or tissue model calculation) and calculate the estimated energy transfer may be performed independently by one of charging device 20 or IMD 14 and/or collectively through communication between charging device 20 and IMD 14.

As described herein, information may be transmitted between charging device 20 and IMD 14. Therefore, IMD 14 and charging device 20 may communicate via wireless communication using any techniques known in the art. Examples of communication techniques may include, for example, low frequency or radiofrequency (RF) telemetry, but other techniques are also contemplated. In some examples, charging device 20 may include a communication head that may be placed proximate to the patient's body near the IMD 14 implant site in order to improve the quality or security of communication between IMD 14 and charging device 20. Communication between charging device 20 may occur during or separate from power transmission.

The estimated energy transfer is a metric that may reflect at least in part the amount of energy absorbed by tissue of patient 12 generated due to the transcutaneous recharge induced electromagnetic energy absorption in tissue. The energy absorbed by tissue of patient 12 may only be significant at or above a certain operating frequency of the primary coil. As the secondary coil in IMD 14 decreases in size to facilitate smaller IMD housing designs, higher frequencies (and smaller wavelengths) of electromagnetic energy may be used to energize the secondary coil. As the frequency of the electromagnetic energy increases, the electric field induced in tissue of a patient increases, which causes a higher specific absorption rate or ohmic losses in tissue. Therefore, more energy is absorbed by tissue of patient 12 at higher frequencies produced by the primary coil. The operating frequency may be predetermined for external charging device 20 and/or IMD 14, such as determined by the size and/or configuration of the primary and/or secondary coils. In other examples, the operating frequency may be adjustable and/or determined by external charging device 20 and/or IMD 14. Generally, electromagnetic energy generated by the primary coil between approximately 10 KHz and 90 KHz may produce negligible specific absorption rates in tissue. However, electromagnetic energy having frequencies between approximately 100 KHz and 90 MHz may elicit specific absorption rates in tissue that cause appreciable amounts of energy to be absorbed by the tissue. In these circumstances, it may be beneficial to monitor the energy transferred to tissue for purposes of controlling subsequent charging, in some examples.

The estimated energy transfer may be utilized by system 10 to control the power transmitted from charging device 20 to IMD 14, the rate of recharging rechargeable power source 18, and the heat generated by IMD 14 during the recharging process. Accordingly, system 10, e.g., one or more processors of charging device 20 and/or IMD 14, may calculate an estimated energy transfer delivered to patient 12 during charging of rechargeable power source 18 of IMD 14 over a period of time. The one or more processors of system 10 may then select a power level for subsequent charging of the rechargeable power source based on the calculated estimated energy transfer. Charging device 20 may then charge rechargeable power source 18 with the selected power level. As discussed in greater detail below, the selected power level may change during the charging session to control the estimated energy transfer to tissue surrounding IMD 14. Although a processor of IMD 14 may select the charging power level, a processor of charging device 20 will be described herein as selecting the charging power level for purposes of illustration.

In one example, charging device 20 may select a high power level when the estimated energy transfer has not exceeded an energy transfer threshold and select a low power level when the estimated energy transfer has exceeded the energy transfer threshold. In this manner, the high power level may charge rechargeable power source 18 at a high rate to reduce charging time while increasing the temperature of IMD 14. Once the estimated energy transfer exceeds the energy transfer threshold, charging device 20 may select a low power level to charge rechargeable power source 18 at a slower rate to reduce the temperature of IMD 14 and reduce the energy transferred to tissue of patient 14. The low power level may be sufficiently minimal so that any increase in temperature of IMD 14 may have minimal or no effect on surrounding tissue.

A high power level and a low power level may be subjective and relative to the charging power that charging device 20 is capable of generating and transmitting to IMD 14. In some cases, the high power level may be the maximum power that charging device 20 can generate. This high power level may be referred to as a "boost" or "accelerated" charging level because of the high rate of charge induced in rechargeable power source 18. This high rate of charge may minimize the amount of time patient 12 needs to recharge rechargeable power source 18. By monitoring the estimated energy transfer, charging device 20 may charge rechargeable power source 18 with the high power level for a longer period of time without damaging tissue surrounding IMD 14. In other words, merely estimating the amount of time that charging device 20 can charge at the high power level without determining the estimated energy transfer may expose tissue to an unsafe level of heat or underutilize the high power charging, resulting in longer total charge times. Therefore, estimating the energy transfer to tissue of patient 12 may allow system 10 to more effectively balance fast charge times and safe heating levels.

In one example, the high power level may be approximately 2.5 Watts and the low power level may be approximately 1.0 milliwatts (mW). An example charge current level may be approximately 100 milliamps (mA) for the high power level and approximately 60 mA for the low power level. The frequency of the charging signal may be independent of the power level, but the pulse width may generally increase with higher power levels assuming a constant H-bridge voltages. An H-bridge circuit may be used as one method to drive the primary coil of charging device 20 with an alternating current. An H-bridge circuit may have alternating pairs of switches (e.g., transistors) which may be gated on and off using pulses. For example, the width of such pulses may be approximately 4000 microseconds (µS) for a high power level and approximately 2000 µS for a low power level with an H-bridge voltage of approximately 10 volts (V). An example primary coil voltage and current for a high power may be approximately 450 V and approximately 800 mA, respectively, and an example primary coil voltage and current for a low power level may be approximately 250 V and approximately 500 mA. These values are merely examples, and other examples, may include higher or lower values in accordance with the techniques described herein.

The energy transfer threshold or limit may be the maximum estimated energy transfer identified as still being safe to patient 12. In other words, the energy transfer threshold may be established or selected to prevent tissue from being heated to an elevated level and duration that could be uncomfortable or undesirable. The energy transfer threshold may be preset by the manufacturer or selected by a clinician.

The energy transfer threshold may also be modified over time as needed. In some examples, the energy transfer threshold may not be set to the maximum safe energy transfer. Instead, the energy transfer threshold may be set to a lower value to establish a safety margin below the energy transfer threshold that minimizes potential overheating of tissue.

The energy transfer threshold may be based on the rate of heat transferred. In other words, the energy transfer threshold may be expressed as mW, and defined as joules per second. In one example, the energy transfer threshold may be selected as the rate of heat transferred to tissue at 50 mW. In another example, the energy transfer threshold may be selected as the rate of heat transferred to tissue at 70 mW. In an alternative example, the energy transfer threshold may be selected as the rate of heat transferred to tissue at 150 mW. These thresholds may be individually compared to the estimated energy transfer, which the estimated rate of heat transferred.

Although charging device 20 may select between two power levels based on the estimated energy transfer, charging device 20 may select between three or more discrete power levels or select the power level from a continual range of available power levels. For example, charging device 20 may select between a high, medium, low, and zero (e.g., no transmitted power) power levels to minimize charging times and minimize uncomfortable or undesirable temperatures in surrounding tissue. In another example, charging device 20 may continually adjust the power level in small increments, where the increments are established by the available resolution of the current able to be generated in the primary coil of charging device 20. Therefore, these more adjustable power levels may result in a power level curve over time as opposed to individual steps in power levels that would be present using only high and low power levels. In any example, the transmitted power from charging device 20 to IMD 14 may be varied based on the determined estimated energy transfer.

In another example, charging device 20 may select a zero power level when the estimated energy transfer has exceeded the energy transfer threshold. This zero power level would stop charging rechargeable power source 18 because charging device 20 would terminate current to the primary coil in response to the selection of the zero power level. Although low power levels may be used to charge rechargeable power source 18 at low rates (e.g., a trickle charge), terminating charging with the zero power level may allow IMD 14 to cool down at the fastest rate and minimize any additional heating of tissue surrounding IMD 14. In addition, the zero power level may be selected when rechargeable power source 18 has been fully charged.

In an additional example, charging device 20 may reduce charging power levels in anticipation of meeting or exceeding the energy transfer threshold. Charging device 20 may calculate an available energy transfer by subtracting the estimated energy transfer from the energy transfer threshold. In other words, the available energy transfer may be the milliwatts (mW) remaining before the estimated energy transfer exceeds the energy transfer threshold. This available energy transfer may be used to reduce power levels of charging prior to exceeding the energy transfer threshold. The available energy transfer may be compared to a high power transfer requirement that indicates the power should be reduced because the estimated energy transfer is approaching the energy transfer threshold. The high power transfer requirement may be set to a percentage of the energy transfer threshold, e.g., between 70 percent and 95 percent of the energy transfer threshold. The high power transfer requirement may instead be set to a certain absolute value below the energy transfer threshold. Using these guidelines, charging device 20 may select a high power level when the available energy transfer is greater than the high power transfer requirement. Charging device 20 may then select a low power level when the available energy transfer is less than the high power transfer requirement. Charging device 20 may subsequently continue to charge rechargeable power source 18 with the low power level or even terminate charging once the estimated energy transfer exceeds the energy transfer threshold.

In some examples, IMD 14 may directly adjust the power level for charging (e.g., limit the charge current) instead of relying on a change in power level at charging device 20. For example, IMD 14 may employ a circuit that may change from full-wave rectification to half-wave rectification to reduce the charge rate and temperature of IMD 14 during charging. In other words, IMD 14 may utilize half-wave rectification as a means to reduce the electrical current delivered to rechargeable power supply 18 instead of reducing the overall power received by IMD 14. Alternatively, IMD 14 may employ other mechanisms such as current and/or voltage limiters that may limit the charging rate of rechargeable power supply 18.

Although an implantable rechargeable power source 18 is generally described herein, techniques of this disclosure may also be applicable to a rechargeable power source 18 that is not implanted. For example, rechargeable power source 18 may be external to the skin of patient 12 and in physical contact with the skin. Therefore, charging device 20 may control the charging of rechargeable power source 18 with the calculated estimated energy transfer even when the power source is external to patient 12. However, tissue models and thresholds may be modified to configure charging device 20 for external charging use.

Figure 2:
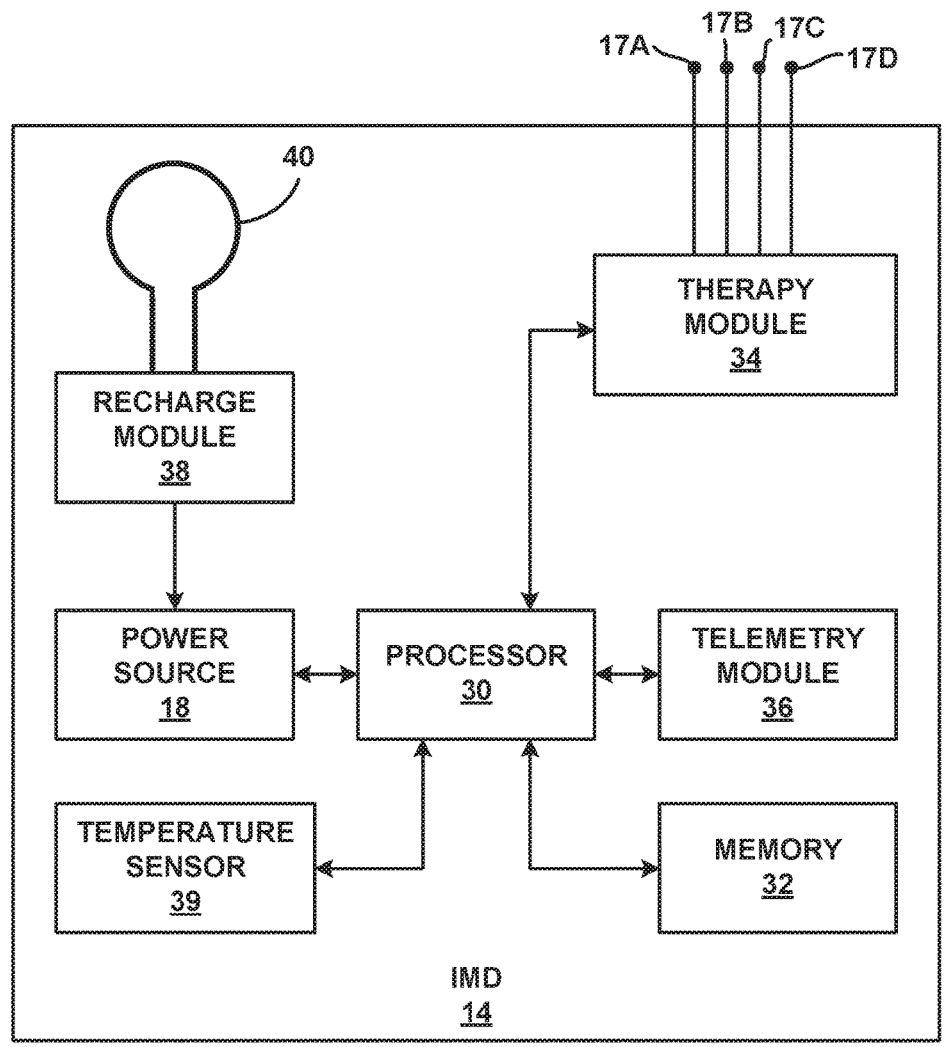
FIG. 2 is a block diagram of the example IMD of FIG. 1.

FIG. 2 is a block diagram illustrating example components of IMD 14. In the example of FIG. 2, IMD 14 includes temperature sensor 39, coil 40, processor 30, therapy module 34, recharge module 38, memory 32, telemetry module 36, and rechargeable power source 18. In other examples, IMD 14 may include a greater or fewer number of components. For example, in some examples, such as examples in which tissue temperature is calculated from the transmitted power, IMD 14 may not include temperature sensor 39.

In general, IMD 14 may comprise any suitable arrangement of hardware, alone or in combination with software and/or firmware, to perform the various techniques described herein attributed to IMD 14 and processor 30. In various examples, IMD 14 may include one or more processors 30, such as one or more microprocessors, digital signal processors (DSPs), application specific integrated circuits (ASICs), field programmable gate arrays (FPGAs), or any other equivalent integrated or discrete logic circuitry, as well as any combinations of such components. IMD 14 also, in various examples, may include a memory 32, such as random access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them. Moreover, although processor 30, therapy module 34, recharge module 38, and telemetry module 36 are described as separate modules, in some examples, processor 30, therapy module 34, recharge module 38, and telemetry module 36 are functionally integrated.

In some examples, processor 30, therapy module 34, recharge module 38, and telemetry module 36 correspond to individual hardware units, such as ASICs, DSPs, FPGAs, or other hardware units.

Memory 32 may store therapy programs or other instructions that specify therapy parameter values for the therapy provided by therapy module 34 and IMD 14. In some examples, memory 32 may also store temperature data from temperature sensor 39, instructions for recharging rechargeable power source 18, circuit models, open-circuit voltage models, tissue models, thresholds, instructions for communication between IMD 14 and charging device 20, or any other instructions required to perform tasks attributed to IMD 14. In this manner, memory 32 may be configured to store a tissue model such that processor 30 may be configured to calculate tissue temperature surrounding IMD 14 based on the tissue model and the power received by secondary coil 40 and rechargeable power source 18 over a period of time. In some examples, memory 32 may be configured to store data representative of an energy absorption tissue model used by processor 30 to determine the energy absorption of tissue at a particular operating frequency. In some examples, memory 32 may be configured to store an open-circuit voltage lookup table with data representative of open-circuit voltage of power source 18 at a particular state-of-charge (SOC). The open-circuit voltages of the lookup table may, in some examples, also be based on the age of the battery of power source 18 or other factors that may affect the open-circuit voltage. In these examples, processor 30 may use the open-circuit voltage lookup table to determine the open-circuit voltage, the effective power delivered to power source 18, and the resistive heat loss from power source 18 at any given SOC of power source 18. In some examples, memory 32 may also be configured to store data of a Thevenin equivalent circuit that is modeled on power source 18.

Generally, therapy module 34 may generate and deliver electrical stimulation under the control of processor 30. In some examples, processor 30 controls therapy module 34 by accessing memory 32 to selectively access and load at least one of the stimulation programs to therapy module 34. For example, in operation, processor 30 may access memory 32 to load one of the stimulation programs to therapy module 34. In such examples, relevant stimulation parameters may include a voltage amplitude, a current amplitude, a pulse rate, a pulse width, a duty cycle, or the combination of electrodes 17A, 17B, 17C, and 17D that therapy module 34 uses to deliver the electrical stimulation signal. Although therapy module 34 may be configured to generate and deliver electrical stimulation therapy via one or more of electrodes 17A, 17B, 17C, and 17D of lead 16, therapy module 34 may be configured to provide different therapy to patient 12. For example therapy module 34 may be configured to deliver drug delivery therapy via a catheter. These and other therapies may be provided by IMD 14.

IMD also includes components to receive power from charging device 20 to recharge rechargeable power source 18 when rechargeable power source 18 has been at least partially depleted. As shown in FIG. 2, IMD 14 includes secondary coil 40 and recharge module 38 coupled to rechargeable power source 18. Recharge module 38 may be configured to charge rechargeable power source 18 with the selected power level determined by either processor 30 or charging device 20. Although processor 30 may provide some commands to recharge module 38 in some examples, processor 30 may not need to control any aspect of recharging.

Secondary coil 40 may include a coil of wire or other device capable of inductive coupling with a primary coil disposed external to patient 12. Although primary coil 48 is illustrated as a simple loop of in FIG. 3, primary coil 48 may include multiple turns of wire. Secondary coil may include a winding of wire configured such that an electrical current can be induced within secondary coil 40 from a magnetic field. The induced electrical current may then be used to recharge rechargeable power source 18. In this manner, the electrical current may be induced in secondary coil 40 associated with rechargeable power source 18. The induction may be caused by electrical current generated in the primary coil of charging device 20 and based on the selected power level. The coupling between secondary coil 40 and the primary coil of charging device 20 may be dependent upon the alignment of the two coils. Generally, the coupling efficiency increases when the two coils share a common axis and are in close proximity to each other. Charging device 20 and/or IMD 14 may provide one or more audible tones or visual indications of the alignment.

Although inductive coupling is generally described as the method for recharging rechargeable power source 18, other wireless energy transfer techniques may alternatively be used. Any of these techniques may generate heat in IMD 14 such that the charging process can be controlled using the calculated estimated energy transfer as feedback.

Recharge module 38 may include one or more circuits that filter and/or transform the electrical signal induced in secondary coil to an electrical signal capable of recharging rechargeable power source 18. For example, in alternating current induction, recharge module 38 may include a half-wave rectifier circuit and/or a full-wave rectifier circuit configured to convert alternating current from the induction to a direct current for rechargeable power source 18. The full-wave rectifier circuit may be more efficient at converting the induced energy for rechargeable power source 18. However, a half-wave rectifier circuit may be used to store energy in rechargeable power source 18 at a slower rate. In some examples, recharge module 38 may include both a full-wave rectifier circuit and a half-wave rectifier circuit such that recharge module 38 may switch between each circuit to control the charging rate of rechargeable power source 18 and temperature of IMD 14.

In some examples, recharge module 38 may include a measurement circuit configured to measure the current and/or voltage induced during inductive coupling. This measurement may be used to measure or calculate the power transmitted to power source 18 of IMD 14 from charging device 20. In some examples, the transmitted power may be used to calculate the estimated energy transfer, which may be used to approximate the temperature of IMD 14 and that of the surrounding tissue. This method may be used to indirectly measure the temperature of tissue in contact with the housing of IMD 14. In some examples, recharge module 38 or other module may include an electrometer or kilometer, which may measure the charge current being applied to rechargeable power source 18 and communicate this charge current to processor 30.

Rechargeable power source 18 may include one or more capacitors, batteries, and/or other energy storage devices. Rechargeable power source 18 may then deliver operating power to the components of IMD 14. In some examples, rechargeable power source 18 may include a power generation circuit to produce the operating power. Rechargeable power source 18 may be configured to operate through hundreds or thousands of discharge and recharge cycles. Rechargeable power source 18 may also be configured to provide operational power to IMD 14 during the recharge process. In some examples, rechargeable power source 18 may be constructed with materials to reduce the amount of heat generated during charging. In other examples, IMD 14 may be constructed of materials that may help dissipate generated heat at rechargeable power source 18, recharge module 38, and/or secondary coil 40 over a larger surface area of the housing of IMD 14.

Although rechargeable power source 18, recharge module 38, and secondary coil 40 are shown as contained within the housing of IMD 14, at least one of these components may be disposed outside of the housing. For example, secondary coil 40 may be disposed outside of the housing of IMD 14 to facilitate better coupling between secondary coil 40 and the primary coil of charging device 20. These different configurations of IMD 14 components may allow IMD 14 to be implanted in different anatomical spaces or facilitate better inductive coupling alignment between the primary and secondary coils.

IMD 14 may also include temperature sensor 39. Temperature sensor 39 may include one or more temperature sensors (e.g., thermocouples or thermistors) configured to measure the temperature of IMD 14. Temperature sensor 39 may be disposed internal of the housing of IMD 14, contacting the housing, formed as a part of the housing, or disposed external of the housing. As described herein, temperature sensor 39 may be used to directly measure the temperature of IMD 14 and/or tissue surrounding and/or contacting the housing of IMD 14. Processor 30, or charging device 20, may use this temperature measurement as tissue temperature feedback to determine the estimated energy transfer provided to tissue during charging of rechargeable power source 18. Although a single temperature sensor may be adequate, multiple temperature sensors may provide a better temperature gradient or average temperature of IMD 14. The various temperatures of IMD 14 may also be modeled and provided to determine the estimated energy transfer to tissue of patient 12. Although processor 30 may continually measure temperature using temperature sensor 39, processor 30 may conserve energy by only measuring temperature during recharge sessions. Further, temperature may be sampled at a rate necessary to calculate the estimated energy transfer, but the sampling rate may be reduced to conserve power as appropriate.

Processor 30 may also control the exchange of information with charging device 20 and/or an external programmer using telemetry module 36. Telemetry module 36 may be configured for wireless communication using radio frequency protocols or inductive communication protocols. Telemetry module 36 may include one or more antennas configured to communicate with charging device 20, for example. Processor 30 may transmit operational information and receive therapy programs or therapy parameter adjustments via telemetry module 36. Also, in some examples, IMD 14 may communicate with other implanted devices, such as stimulators, control devices, or sensors, via telemetry module 36. In addition, telemetry module 36 may be configured to transmit the measured tissue temperatures from temperature sensor 39, the determined resistive heat loss from power source 18, and/or the determined energy absorbed by tissue of patient 12, for example. In some examples, tissue temperature may be measured adjacent to rechargeable power source 18. In this manner, charging device 20 may compare the estimated energy transfer with the transmitted tissue temperature. In other examples, processor 30 may calculate the estimated energy transfer and transmit the calculated estimated energy transfer using telemetry module 36.

In other examples, processor 30 may transmit additional information to charging device 20 related to the operation of rechargeable power source 18. For example, processor 30 may use telemetry module 36 to transmit indications that rechargeable power source 18 is completely charged, rechargeable power source 18 is fully discharged, how much charge (e.g., the charge current) is being applied to rechargeable power source 18, the charge capacity of rechargeable power source 18, the state-of-charge (SOC) of rechargeable power source 18, or any other charge information of rechargeable power source 18. Processor 30 may also transmit information to charging device 20 that indicates any problems or errors with rechargeable power source 18 that may prevent rechargeable power source 18 from providing operational power to the components of IMD 14.

Figure 3:
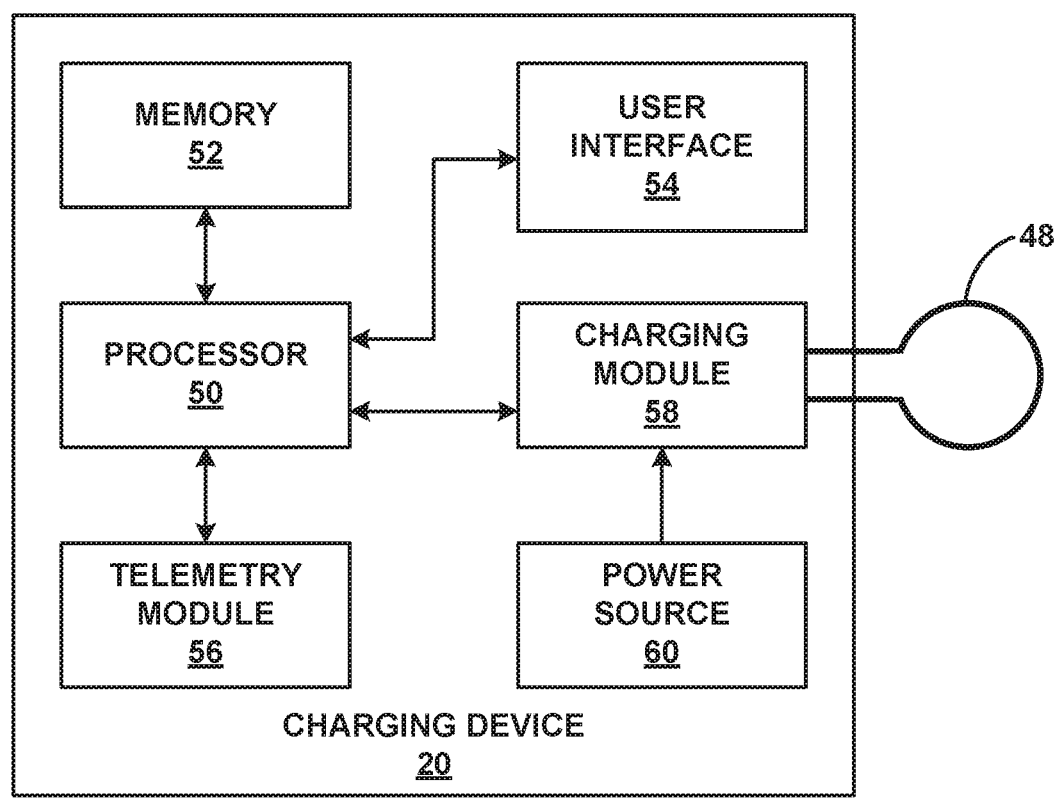
FIG. 3 is a block diagram of the example external charging device of FIG. 1.

FIG. 3 is a block diagram of the example external charging device 20. While charging device 20 may generally be described as a hand-held device, charging device 20 may be a larger portable device or a more stationary device. In addition, in other examples, charging device 20 may be included as part of an external programmer or include functionality of an external programmer. In addition, charging device 20 may be configured to communicate with an external programmer. As illustrated in FIG. 3, charging device 20 may include a processor 50, memory 52, user interface 54, telemetry module 56, power module 58, coil 48, and power source 60. Memory 52 may store instructions that, when executed by processor 50, cause processor 50 and external charging device 20 to provide the functionality ascribed to external charging device 20 throughout this disclosure.

In general, charging device 20 comprises any suitable arrangement of hardware, alone or in combination with software and/or firmware, to perform the techniques attributed to charging device 20, and processor 50, user interface 54, telemetry module 56, and charging module 58 of charging device 20. In various examples, charging device 20 may include one or more processors, such as one or more microprocessors, DSPs, ASICs, FPGAs, or any other equivalent integrated or discrete logic circuitry, as well as any combinations of such components. Charging device 20 also, in various examples, may include a memory 52, such as RAM, ROM, PROM, EPROM, EEPROM, flash memory, a hard disk, a CD-ROM, comprising executable instructions for causing the one or more processors to perform the actions attributed to them. Moreover, although processor 50 and telemetry module 56 are described as separate modules, in some examples, processor 50 and telemetry module 56 are functionally integrated. In some examples, processor 50 and telemetry module 56 and charging module 58 correspond to individual hardware units, such as ASICs, DSPs, FPGAs, or other hardware units.

Memory 52 may store instructions that, when executed by processor 50, cause processor 50 and charging device 20 to provide the functionality ascribed to charging device 20 throughout this disclosure. For example memory 52 may include instructions that cause processor 50 to calculate estimated energy transfers, establish thresholds, select power levels based on the estimated energy transfers and otherwise control charging module 58, communicate with IMD 14, or instructions for any other functionality. In addition, memory 52 may include a record of selected power levels, calculated estimated energy transfers, or any other data related to charging rechargeable power source 18.

Processor 50 may, when requested, transmit any of this stored data in memory 52 to another computing device for review or further processing.

In some examples, memory 52 may be configured to store an open-circuit voltage lookup table with data representative of open-circuit voltage of power source 18 at a particular state-of-charge (SOC), age of power source 18, and/or any other factors that may affect the open-circuit voltage. In these examples, processor 50 may use the open-circuit voltage lookup table to determine the open-circuit voltage and then use the open-circuit voltage to determine an estimated power stored in (e.g., an effective power delivered to) power source 18. This open-circuit voltage may be used to determine the resistive heat loss from power source 18 at any given SOC of power source 18. In some examples, memory 52 may also be configured to store data of a Thevenin equivalent circuit that is modeled on power source 18. In some examples, memory 52 may be configured to store data representative of an energy absorption tissue model used by processor 50 to determine the energy absorption of tissue at a particular operating frequency. In some examples, memory 52 may be configured to store data representative of a tissue model used by processor 50 to calculate tissue temperature based on tissue model and power transmitted to rechargeable power source 18 over a period of time. Tissue model may indicate how temperate of tissue surrounding IMD 14 changes over time based on, i.e., as a function of, the estimated energy transfer. Therefore, processor 50 may be able to estimate tissue temperature without direct measurement of the temperature of tissue surrounding the housing of IMD 14.

User interface 54 may include a button or keypad, lights, a speaker for voice commands, a display, such as a liquid crystal (LCD), light-emitting diode (LED), or cathode ray tube (CRT). In some examples the display may be a touch screen. As discussed in this disclosure, processor 50 may present and receive information relating to the charging of rechargeable power source 18 via user interface 54. For example, user interface 54 may indicate when charging is occurring, quality of the alignment between coils 40 and 48, the selected power level, current charge level of rechargeable power source 18, duration of the current recharge session, anticipated remaining time of the charging session, or any other information. Processor 50 may receive some of the information displayed on user interface 54 from IMD 14 in some examples.

User interface 54 may also receive user input via user interface 54. The input may be, for example, in the form of pressing a button on a keypad or selecting an icon from a touch screen. The input may request starting or stopping a recharge session, a desired level of charging, or one or more statistics related to charging rechargeable power source 18 (e.g., the estimated energy transfer). In this manner, user interface 54 may allow the user to view information related to the charging of rechargeable power source 18 and/or receive charging commands.

Charging device 20 also includes components to transmit power to recharge rechargeable power source 18 associated with IMD 14. As shown in FIG. 3, charging device 20 includes primary coil 48 and charging module 58 coupled to power source 60. Charging module 58 may be configured to generate an electrical current in primary coil 48 from voltage stored in power source 60. Although primary coil 48 is illustrated as a simple loop in FIG. 3, primary coil 48 may include multiple turns of wire. Charging module 58 may generate the electrical current according to a power level selected by processor 50 based on the estimated energy transfer. As described herein, processor 50 may select a high power level, low power level, or a variety of different power levels to control the rate of recharge in rechargeable power source 18 and the temperature of IMD 14. In some examples, processor 50 may control charging module 58 based on a power level selected by processor 30 of IMD 14.

Primary coil 48 may include a coil of wire, e.g., having multiple turns, or other device capable of inductive coupling with a secondary coil 40 disposed within patient 12. Primary coil 48 may include a winding of wire configured such that an electrical current generated within primary coil 48 can produce a magnetic field configured to induce an electrical current within secondary coil 40. Primary coil 48 may be constructed of certain dimensions and/or driven to produce electromagnetic energy of a particular frequency selected for secondary coil 40. The induced electrical current may then be used to recharge rechargeable power source 18. In this manner, the electrical current may be induced in secondary coil 40 associated with rechargeable power source 18. The coupling efficiency between secondary coil 40 and primary coil 48 of charging device 20 may be dependent upon the alignment of the two coils. Generally, the coupling efficiency increases when the two coils share a common axis and are in close proximity to each other. User interface 54 of charging device 20 may provide one or more audible tones or visual indications of the alignment.

Charging module 58 may include one or more circuits that generate an electrical signal, and an electrical current, within primary coil 48. Charging module 58 may generate an alternating current of specified amplitude and frequency in some examples. In other examples, charging module 58 may generate a direct current. In any case, charging module 58 may be capable of generating electrical signals, and subsequent magnetic fields, to transmit various levels of power to IMD 14. In this manner charging module 58 may be configured to charge rechargeable power source 18 of IMD 14 with the selected power level.

The power level that charging module 58 selects for charging may be used to vary one or more parameters of the electrical signal generated for coil 48. For example, the selected power level may specify a wattage, electrical current of primary coil 48 or secondary coil 40, current amplitude, voltage amplitude, pulse rate, pulse width, or any other parameter that may be used to modulate the power transmitted from coil 48. In this manner, each power level may include a specific parameter set that specifies the signal for each power level. Changing from one power level to another power level, e.g., a high power level to a low power level, may include adjusting one or more parameters. The parameters of each power level may be selected based on hardware characteristics of charging device 20 and/or IMD 14.

Power source 60 may deliver operating power to the components of charging device 20. Power source 60 may also deliver the operating power to drive primary coil 48 during the charging process. Power source 60 may include a battery and a power generation circuit to produce the operating power. In some examples, the battery may be rechargeable to allow extended portable operation. In other examples, power source 60 may draw power from a wired voltage source such as a consumer or commercial power outlet.

Although power source 60 and charging module 58 are shown within a housing of charging device 20, and primary coil 48 is shown external to charging device 20, different configurations may also be used. For example, primary coil 48 may also be disposed within the housing of charging device 20. In another example, power source 60, charging module 58, and primary coil 48 may be all located external to the housing of charging device 20 and coupled to charging device 20.

Telemetry module 56 supports wireless communication between IMD 14 and charging device 20 under the control of processor 50. Telemetry module 56 may also be configured to communicate with another computing device via wireless communication techniques, or direct communication through a wired connection. In some examples, telemetry module 56 may be substantially similar to telemetry module 36 of IMD 14 described herein, providing wireless communication via an RF or proximal inductive medium. In some examples, telemetry module 56 may include an antenna, which may take on a variety of forms, such as an internal or external antenna.

Examples of local wireless communication techniques that may be employed to facilitate communication between charging device 20 and IMD 14 include RF communication according to the 802.11 or Bluetooth specification sets or other standard or proprietary telemetry protocols. In this manner, other external devices may be capable of communicating with charging device 20 without needing to establish a secure wireless connection. As described herein, telemetry module 56 may be configured to receive a measured tissue temperature, a determined resistive heat loss from power source 18, determined energy absorption of tissue of patient 12, a determined estimated energy transfer, and/or any other information relevant to determining the estimated energy transfer from IMD 14.

In some examples, tissue temperature may be measured adjacent to rechargeable power source 18, such as near the housing of IMD 14 or external of the housing. Although IMD 14 may measure tissue temperature, one or more different implantable temperature sensors (e.g., standalone implantable temperature sensing devices) may independently measure tissue temperature at different positions and transmit the temperature to charging device 20. In some examples, multiple temperature readings by IMD 14 may be averaged or otherwise used to produce a single temperature value that is transmitted to charging device 20. The temperature may be sampled and/or transmitted at different rates, e.g., on the order of microseconds, milliseconds, seconds, minutes, or even hours.

Figure 4:
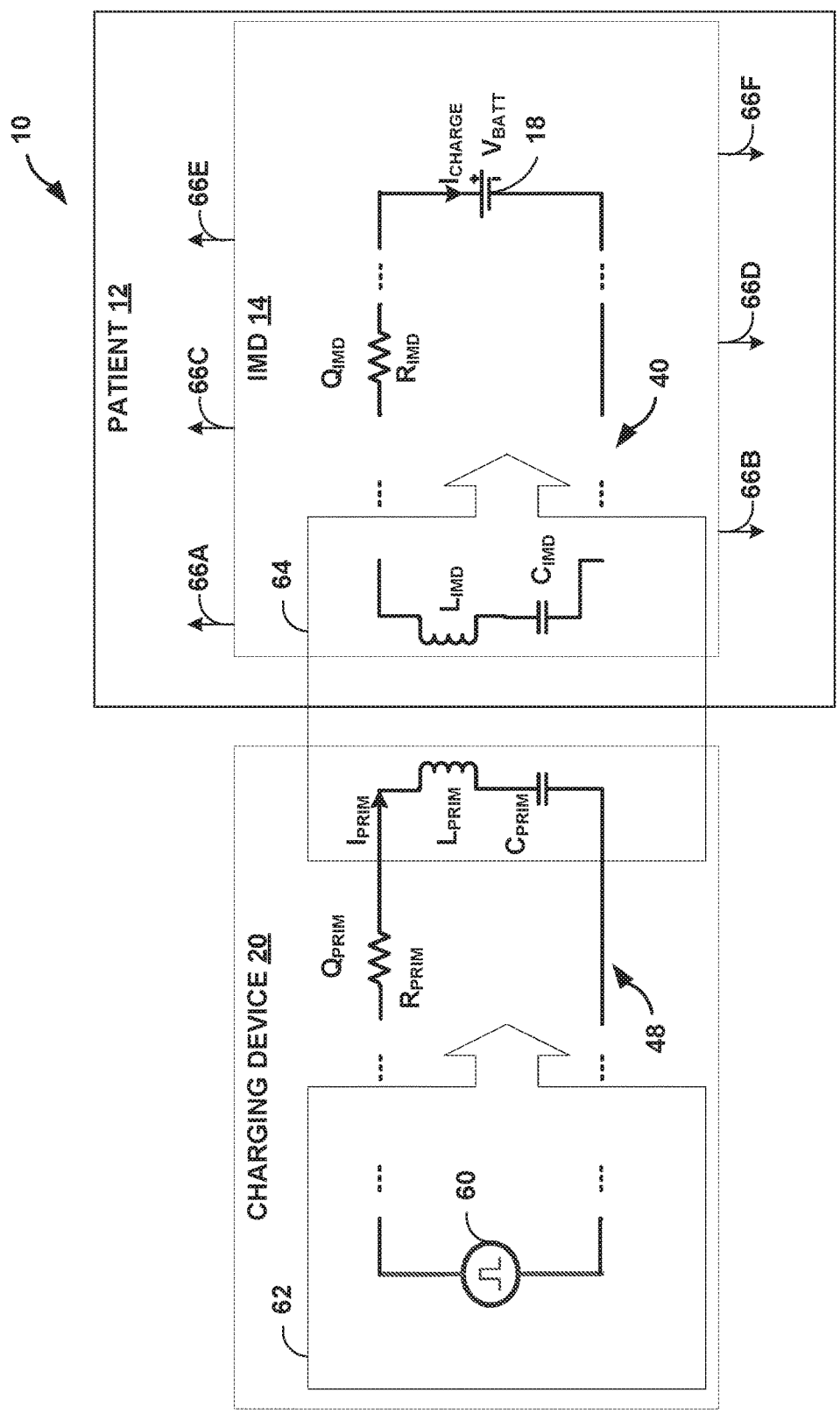
FIG. 4 is a schematic diagram that illustrates an example of the power delivered to the primary coil and the power delivered to charge a rechargeable power source of an IMD.

FIG. 4 is a schematic diagram that illustrates an example of power 62 delivered to primary coil 48 and power 64 delivered to charge rechargeable power source 18 of IMD 14. FIG. 4 is described with reference to FIGS. 1-3. In the example of FIG. 4, system 10 including patient 12, IMD 14, and charging device 20 may correspond to system 10 including patient 12, IMD 14, and charging device 20 as described in FIG. 1. In the example of FIG. 4, IMD 14 includes power source 18 and secondary coil 40 may correspond to IMD 14. Charging device 20 includes primary coil 48 and power source 60. System 10 may also include $Q_{PRIM}$, $R_{PRIM}$, $L_{PRIM}$, $C_{PRIM}$, $Q_{IMD}$, $R_{IMD}$, $L_{IMD}$, $C_{IMD}$, $I_{CHARGE}$, $V_{BATT}$, power 62, power 64, and IMD energy transfer 66A-66F (collectively "IMD energy transfer 66").

$Q_{PRIM}$ is the electrical heat loss caused by the resistance $R_{PRIM}$ in charging device 20. The tank circuit of primary coil 48 also includes $I_{PRIM}$, $L_{PRIM}$, and $C_{PRIM}$. $I_{PRIM}$ is the current generated through the tank circuit of primary coil 48. $L_{PRIM}$ is the inductance in the tank circuit of primary coil 48. $C_{PRIM}$ is the capacitance in the tank circuit of primary coil 48.

$Q_{IMD}$ is the electrical heat loss caused by the resistance $R_{IMD}$) in one or more circuits between secondary coil 40 and power source 18 of IMD 14. The tank circuit of secondary coil 40 also includes $L_{IMD}$ and $C_{IMD}$. $L_{IMD}$ is the inductance in the tank circuit of secondary coil 40. $C_{IMD}$ is the capacitance in the tank circuit of secondary coil 40. $I_{CHARGE}$ is the charge current generated in secondary coil 40 and delivered to power source 18 of IMD 14. $V_{BATT}$ is the loaded voltage measured across the terminals of power source 18.

Power 62 is the total power delivered to the tank circuit of primary coil 48 from power source 60 of charging device 20. Power 64 is the total power delivered to IMD 14 from inductive coupling between charging device 20 and IMD 14. In other words, power 64 is the total power delivered to IMD 14 from the current $I_{PRIM}$ delivered to primary coil 48 from power source 60 of charging device 20, which induces the current $I_{CHARGE}$ in secondary coil 40 and recharges the rechargeable power source 18 of IMD 14. IMD energy transfer 66 is the energy transferred from IMD 14 to tissue of patient 12 and is calculated, or estimated, as described herein. In some examples, the estimated IMD energy transfer 66 may be substantially similar to the actual energy transferred to tissue of patient 12. In some examples, IMD energy transfer 66 may be less than the actual energy transferred to tissue of patient 12. In these examples, the estimated energy transferred to tissue of patient 12 may include IMD energy transfer 66 in addition to the resistive heat loss from power source 18 and/or the energy absorbed by tissue of patient 12.

In the example of FIG. 4, an energy balance approach of system 10 may be used to estimate the energy transferred to tissue of patient 12 during recharging of power source 18. For example, the estimated energy transfer may be determined by subtracting the electrical heat loss in primary coil 48 and total power 64 delivered to the battery from the total power 62 delivered to primary coil 48. The estimated energy transfer may be an estimation of the IMD energy transfer 66 to tissue. In some examples, the estimated energy transfer may be represented as Equation 1, where the estimated energy transfer is equal to subtracting the electrical heat losses in primary coil 48 and the total power 64 delivered to power source 18 from the total power 62 delivered to primary coil 48 from power source 60. In Equation 1, Q_transfer is an estimated energy transfer delivered to tissue of patient 12, P_recharge is power 62 delivered to primary coil 48 from power source 60, Q_prim is the electrical heat loss in primary coil 48, and I_charge*V_batt is total power 64 delivered to power source 18. In these examples, I_charge may be the charge current at power source 18 and V_batt may be the loaded voltage across power source 18.

$$Q\_transfer = P\_recharge - Q\_prim - I\_charge * V\_batt \quad (1)$$

In some examples, the energy transfer of system 10 may be estimated using Equation 1 provided impedance-related heat losses of power source 18 are negligible over the life of IMD 14 and the operating frequency of primary coil 48 does not significantly induce any human tissue absorption (e.g., electromagnetic frequencies less than approximately 100 KHz). However, in other examples, where the impedance-related heat losses of power source 18 is not negligible and/or the recharge frequency induces some human tissue absorption of energy, the resistive heat loss from power source 18 and/or any energy absorption in tissue of patient 12 surrounding IMD 14 may be determined and included in the estimation of the estimated energy transfer to tissue of patient 12. In other words, as rechargeable power source 18 decreases in size, the impedance of the electrodes and/or other battery circuitry may increase and cause resistive heat losses significant to energy transferred to patient 12. In addition, the reduction in size of IMD 14 may similarly require a reduction in the size of secondary coil 40 and a similar increase in the recharge frequency (and a decrease in wavelength) of the electromagnetic energy delivered by primary coil 48 to secondary coil 40. This increase in frequency may result in more energy absorbed in tissue of patient 12 that may be included in the estimated energy transfer to tissue.

When the impedance of power source 18 may not negligible (e.g., the electrodes of power source 18 are smaller than the electrodes of larger power sources), the estimated energy transfer of system 10 may be greater than IMD energy transfer 66 that would otherwise be calculated using the loaded voltage of power source 18. In other words, determining only IMD energy transfer 66 as described in the example of FIG. 4 may underestimate the actual energy transfer received by tissue of patient 12. Therefore, the estimated energy transfer may be determined by also including the resistive heat loss from power source 18. The resistive heat loss from power source 18 may thus be included in the energy balance approach. The impedance of power source 18 may be modeled to determine the resistance of power source 18. For example, where power source 18 is a battery, power source 18 may be modeled to determine the Thevenin equivalent circuit of the battery. In this example, the Thevenin equivalent circuit of power source 18 may be represented by Equation 2, where the loaded battery voltage, during the charging of power source 18, is equal to adding the open-circuit voltage and the charge resistance of power source 18. In Equation 2, V_batt is the loaded battery voltage, U_batt is the open-circuit voltage, R_batt is the Thevenin resistance, and I_charge is the charge current applied to the battery. In this example, V_batt may be a function of state of charge (SOC), time (t), and charge current (I_charge), U_batt may be a function of SOC, and charge resistance may be a function of SOC, t, and I_charge.

$$V\_batt(SOC,t,I\_charge)=U\_batt(SOC)+ I\_charge*R\_batt(SOC,t,I\_charge) \quad (2)$$

In this example, the Thevenin equivalent circuit model represents the open-circuit voltage as a function of SOC, and the charge resistance (I_charge*R_batt) as a function of SOC, charge current, and time. In this way, a processor of IMD 14 and/or charging device 20 may determine the SOC of power source 18, and based on the determined SOC also determine the open-circuit voltage of power source 18 from a lookup table, which may enable a determination of the resistive heat loss ($I^2$_charge*R_batt) in power source 18. In some examples, memory 32 of IMD 14, memory 52 of charging device 20, or any other suitable memory may be configured to store the lookup table with the predetermined values of U_batt at respective SOC values of power source 18. Although, the open-circuit voltage as described herein is a function of SOC, in some examples, the open-circuit model may also be a function of time because of the chemistry of power source 18. In these examples, memory 32 of IMD 14, memory 52 of charging device 20, or any other suitable memory may be configured to store the lookup table with the predetermined values of U_batt at respective SOC and time values of power source 18.

In some examples, the determination of the resistive heat loss may also enable a determination of the type of heat equation to use based on the error in the heat estimation. For example, determining the resistive heat loss may allow for a determination of whether Equation 1 provides an estimated energy transfer within an acceptable error level or whether Equation 1 should be modified to account for the resistive heat loss from power source 18.

In some examples, Equation 1 may be modified with Equation 2 to account for the resistive heat loss. In these examples, the estimated energy transfer may be represented as Equation 3, where the estimated energy transfer is equal to subtracting the electrical heat loss of primary coil 48 and the effective power 64 delivered for storage to power source 18 from the total power 62 delivered to primary coil 48, and then adding the resistive heat loss. In these examples, Equation 3 may account for IMD energy transfer 66 in addition to the resistive heat loss from power source 18. In other words, the estimated energy transfer of Equation 3 may be greater than the estimated energy transfer of Equation 1 because of the additional resistive heat loss. Equation 3 is modified from Equation 1. Equation 3 illustrates how an estimated energy transfer delivered to tissue of patient 12 can incorporate the resistive heat losses from power source 18, where Q_transfer does not. P_recharge may be total power 62 delivered to primary coil 48 from power source 60, Q_prim may be the electrical heat loss in primary coil 48, I_charge*U_batt may be the power stored in (or effective power delivered to) power source 18, and $I^2$_charge*R_batt is the resistive heat loss from power source 18. In these examples, I_charge may be the charge current applied to power source 18, U_batt may be the open-circuit voltage of power source 18, and R_batt may be the Thevenin equivalent resistance of power source 18.

$$Q\_transfer=P\_recharge-Q\_prim-I\_charge*U\_batt- I^2\_charge*R\_batt \quad (3)$$

As shown in Equation 3, the I_charge*V_batt term in Equation 1 has been replaced with the I_charge*U_batt and $I^2$ charge*R_batt terms. I_charge*V_batt represents the total energy delivered to power source 18. However, not all of that energy is stored as increased charge in the battery of power source 18. The I_charge*U_batt term more accurately indicates an estimated power stored in power source 18. The remainder of the power delivered is represented as the $I^2$_charge*R_batt which is generally transformed into heat that can be transferred to patient 12. Since Q_transfer and $I^2$_charge*R_batt represent heat transferrable to patient 12, they represent an updated Q'_transfer term. When adding the $I^2$_charge*R_batt term to both sides of Equation 3, Equation 4 can be used to represent the Q'_transfer term that incorporates resistive heat losses from power source 18 into the estimated energy transfer.

$$Q'\_transfer=P\_recharge-Q\_prim-I\_charge*U\_batt \quad (4)$$

In some examples, the resistive heat loss of power source 18 in Equation 3 is the difference between the total power delivered to power source 18 defined by the multiplication of the charge current and the loaded voltage of power source as described in Equation 1, and the effective power delivered to (or estimated stored power in) power source 18 (defined by the multiplication of the charge current and the open-circuit voltage of power source 18 at a particular SOC). In these examples, the resistive heat loss is the multiplication of the charge current and the charge resistance of power source 18, or the charge current squared and the Thevenin equivalent resistance of power source 18. It is noted that Q'_transfer can be determined without calculating the $I^2$_charge*R_batt term when U_batt is estimated and used to estimate the power stored in power source 18 during the charging session. In other words, when both Q_transfer and $I^2$_charge*R_batt are unknown but can be useful as the sum of both terms, separate determination of the $I^2$_charge*R_batt may not be necessary.

In some examples, where the impedance of power source 18 is known to not be negligible, Equations 3 and 4 may provide a more accurate estimation of energy transferred to tissue of patient 12 than Equation 1. In some examples, where the impedance of power source 18 is known, the Q'_transfer of Equation 4 may be equivalent to the Q_transfer of Equation 1 when the impedance of power source 18 ($I^2$_charge*R_batt) is added to Q_transfer of Equation 1 (i.e., adding the impedance of power source 18 to the P_recharge term on the right side of Equation 1). In some examples, where the impedance of power source 18 is known to only be negligible, Equation 3 may still provide a more accurate estimation of the energy transferred to tissue of patient 12 than Equation 1. In some examples, Equation 3 may enable IMD 14, charging device 20, a programmer, or any suitable computing device to determine whether Equation 1 is within acceptable error levels based on the resistive heat loss from power source 18.

In some examples, where the recharge operating frequency of IMD 14 is high enough to induce some human tissue absorption (e.g., electromagnetic energy recharge frequencies greater than 100 KHz), the energy transferred to tissue of patient 12 may be estimated by determining a energy absorption in tissue of patient 12 surrounding IMD 14, and adding the energy absorbed by tissue in the energy balance approach.

In other examples, the estimated energy transfer may be represented as Equation 5, where the estimated energy transfer is equal to subtracting the electrical heat loss of primary coil 48 and the total power 64 delivered to power source 18 from the total power delivered to primary coil 48, and adding the energy absorbed in tissue of patient 12 to the total power delivered to primary coil 48. In these examples, Equation 5 may account for IMD energy transfer 66 in addition to the direct energy absorption in tissue of patient 12 from primary coil 48. In other words, the estimated energy transfer of Equation 5 may be greater than the estimated energy transfer of Equation 1 because of the inclusion of additional energy absorbed in tissue of patient 12. In Equation 5, Q"_transfer may be the estimated energy transferred to tissue of patient 12, P_recharge may be power 62 delivered to primary coil 48 from power source 60, Q_prim may be the electrical heat loss in primary coil 48, I_charge*V_batt may be power 64 delivered to power source 18, and Q_tissue may be the energy absorption of tissue of patient 12.

$$Q''\_transfer = P\_recharge - Q\_prim - I\_charge * V\_batt + Q\_tissue \quad (5)$$

In some examples, Q_tissue may be estimated based on one or more variables including, but not limited to, the frequency of the electromagnetic energy transmitted from primary coil 48 of charging device 20, the energy capacity and/or absorption rate of tissue adjacent IMD 14, density of surrounding tissue, inherent body temperature, estimated surface area of tissue surrounding IMD 14, cross-sectional surface area of IMD 14, depth of IMD 14 from the skin of patient 12, orientation of the secondary coil within patient 12, or any other variable that would affect the energy absorption of tissue surrounding housing of IMD 14 or otherwise exposed to the electromagnetic energy. In some examples, one or more of these variables may be stored in a lookup table and used to calculate Q_tissue with one or more determined variables such as delivered energy and/or the time during which energy was delivered from primary coil 48. In other examples, Q_tissue may be retrieved from a plurality of predetermined values stored in a lookup table (e.g., values retrieved based on one or more variables related to charging). In these examples, memory 32 of IMD 14, memory 52 of charging device 20, or any other suitable memory may be configured to store the lookup table with the variables related to and/or predetermined values of Q_tissue.

In some examples, Q_tissue may be determined based on one or more variables including, but not limited to, the recharge operating frequency of IMD 14 and charging device 20, the energy capacity and/or absorption of tissue adjacent IMD 14, density of surrounding tissue, inherent body temperature, estimated surface area of tissue surrounding IMD 14, cross-sectional surface area of IMD 14, depth of IMD 14 from the skin of patient 12, orientation of the secondary coil within patient 12, or any other variable that would affect the energy absorption of tissue surrounding and/or in immediate contact with the housing of IMD 14. In these examples, processor 30 of IMD 14, processor 50 of charging device 20, or any other suitable processor may be configured to determine the values of Q_tissue.

In some examples, where the recharge operating frequency of IMD 14 and charging device 20 is high enough to cause some energy absorption in tissue of patient 12, Equation 5 may provide a more accurate estimation of the energy transferred to tissue of patient 12 than Equation 1. In some examples, where the energy absorption of tissue is known to be negligible at a particular recharge operating frequency, Equation 5 may be substantially similar to Equation 1. In other words, if the energy absorption of tissue is negligible, the estimated energy transfer may be IMD energy transfer 66 as determined from Equation 1. In other examples, Equation 5 may enable IMD 14, charging device 20, a programmer, or any suitable computing device to determine whether Equation 1 is within acceptable error levels based on the determined energy absorption of tissue of patient 12.

Where the impedance of power source 18 and the energy absorption of tissue of patient 12 may not be negligible, the energy transferred to tissue of patient 12 of system 10 may be further estimated by determining both the resistive heat loss from power source 18 and the energy absorption in tissue of patient 12, and including both determinations in the energy balance approach. For example, the estimated energy transfer may be represented as Equation 6 (e.g., a combination of Equations 4 and 5). The estimated energy transfer may be equal to subtracting the electrical heat loss of primary coil 48 and the estimated power stored to power source 18 from the total power deliver to primary coil 48, and adding the energy absorbed in tissue of patient 12. In this example, the estimated energy transfer may account for IMD energy transfer 66 in addition to the resistive heat loss and the energy absorption in tissue of patient 12. In other words, Equation 6 may be greater than Equation 1 because of the additional resistive heat loss from power source 18 and/or energy absorbed in tissue of patient 12 identified in the calculation. In Equation 6, Q'''_transfer may be the estimated energy transferred to tissue of patient 12, P_recharge may be power 62 delivered to primary coil 48 from power source 60, Q_prim may be the electrical heat loss in primary coil 48, I_charge*U_batt may be effective power delivered to (or estimated power stored in) power source 18, and Q_tissue is the energy absorption of tissue of patient 12. In these examples, I_charge may be the charge current at power source 18, and U_batt may be the open-circuit voltage across power source 18.

$$Q'''\_transfer = P\_recharge - Q\_prim - I\_charge * U\_batt + Q\_tissue \quad (6)$$

In some examples, where the resistive heat loss and/or the energy absorbed in tissue of patient 12 may not be negligible, Equation 6 may provide a more accurate estimation of the energy transferred to tissue of patient 12 than Equation 1. In some examples, where the resistive heat loss and/or the energy absorbed in tissue of patient 12 may be negligible, Equation 5 may be substantially similar to Equations 1-4. In other words, if the resistive heat loss from power source 18 and the energy absorption of tissue is negligible, the estimated energy transfer may be IMD energy transfer 66. In some examples, Equation 6 may enable IMD 14, charging device 20, a programmer, or any suitable computing device to determine whether Equation 1 is within acceptable error levels based on the determined resistive heat loss and the determined energy absorption of tissue of patient 12.

Figure 5:
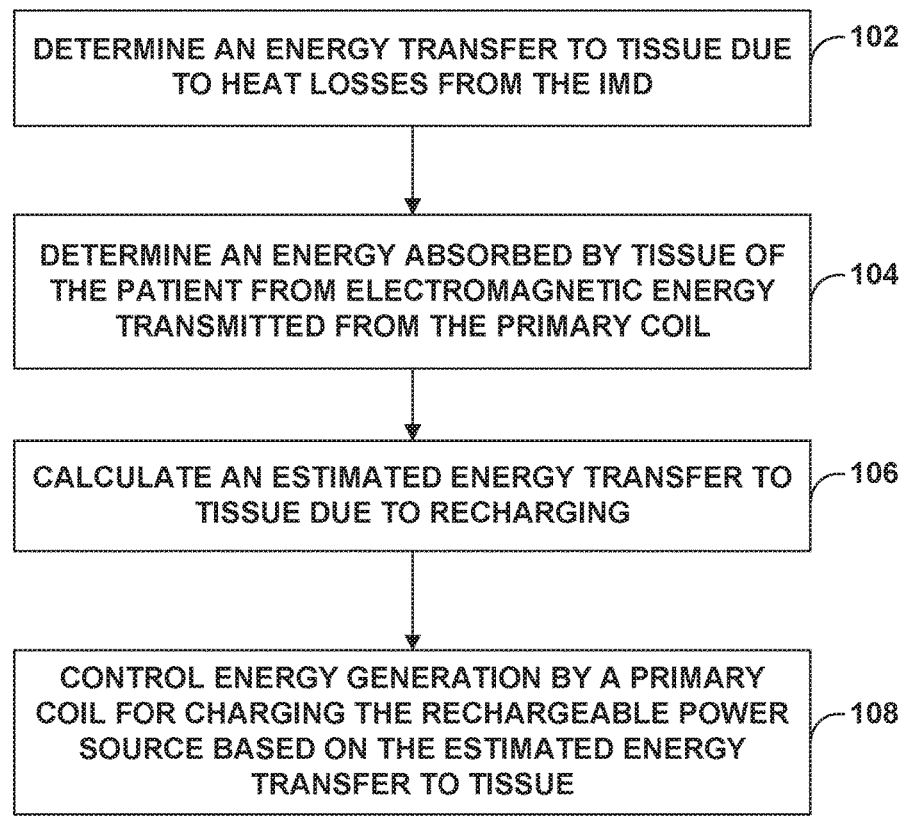
FIG. 5 is a flow diagram that illustrates an example technique for controlling energy generation by the external charging device based on a calculated estimated energy transfer to tissue of a patient.

FIG. 5 is a flow diagram that illustrates an example technique for controlling energy generation by external charging device 20 based on a calculated estimated energy transfer to tissue of a patient. Although processor 50 of charging device 20 will be described as generally performing the technique of FIG. 5, the technique of FIG. 5 may instead be performed by a combination of processors 30 and 50, in other examples.

As shown in FIG. 5, during a charging session for rechargeable power source 18, processor 50 may determine energy transfer to tissue due to heat losses from IMD 14, such as a resistive heat loss from rechargeable power source 18 (102). In one example, processor 50 may determine the energy transfer in step 102 by subtracting the heat loss in the primary coil 48 during charging and the estimated power stored in the rechargeable power source from the power delivered to the primary coil during charging of power source 18. The estimated power stored in power source 18 may be determined by multiplying the charge current by the open-circuit voltage of power source 18. In some examples, processor 50 may determine the resistive heat loss from rechargeable power source 18 by measuring a charge current applied to rechargeable power source 18, measuring a loaded voltage across rechargeable power source 18, determining an open-circuit voltage of rechargeable power source 18, determining a difference between the loaded voltage and the open-circuit voltage, wherein the difference is a voltage due to a charge resistance of rechargeable power source 18, and determining the resistive heat loss from rechargeable power source 18 based on the charge current and the voltage due to the charge resistance of rechargeable power source 18. Determining the estimated power stored in power source 18 may include determining a charge current applied to power source 18 and determining an open-circuit voltage of power source 18, wherein the open-circuit voltage does not incorporate resistance of power source 18 that results in the resistive heat loss when the charge current is applied to power source 18. Processor 50 may determine the open-circuit voltage of rechargeable power source 18 by determining a state of charge of rechargeable power source 18, and determining the open-circuit voltage of rechargeable power source 18 based on the determined state of charge of rechargeable power source 18. In some examples, processor 50 may determine the state of charge of rechargeable power source 18 by measuring with an electrometer an amount of charge applied to rechargeable power source 18, determining a capacity of rechargeable power source 18, and determining the state of charge of rechargeable power source 18 based on the determined amount of charge and the determined amount of capacity of rechargeable power source 18. In some examples, processor 50 may determine the open-circuit voltage of rechargeable power source 18 by determining a state of charge of rechargeable power source 18, determining an age of rechargeable power source 18, and determining the open-circuit voltage of rechargeable power source 18 based on the determined state of charge and the determined age of rechargeable power source 18. In other examples, the open-circuit voltage of rechargeable power source 18 may correspond to thermodynamic voltage of rechargeable power source 18.

Additionally, or alternatively, during a charging session for rechargeable power source 18, processor 50 may determine an estimated energy absorbed by tissue of patient 12 from electromagnetic energy transmitted from the primary coil during charging of rechargeable power source 18 (104). In some examples, processor 50 may determine the estimated energy absorbed by tissue of the patient by determining a current delivered to the primary coil, determining a frequency of the electromagnetic (e.g., radiofrequency) energy emitted by the primary coil, and determining, based on the current delivered to the primary coil and the frequency of the radiofrequency energy emitted by the primary coil, the estimated energy absorbed by tissue of the patient. In some examples, processor 50 may also determine the estimated energy absorbed by tissue of the patient by determining a volume of tissue subjected to absorption of the radiofrequency energy emitted by the primary coil, and determining, based on the area of tissue, the estimated energy absorbed by tissue of the patient.

Processor 50 may then calculate the total estimated energy transfer to tissue of patient 12 due to the recharging session (106). In some examples, calculating the estimated energy transfer to tissue of patient 12 may include the determined resistive heat loss from rechargeable power source 18 and energy directly absorbed by the tissue from primary coil 48. In these examples, processor 50 may calculate the estimated energy transfer by determining a power delivered to the primary coil during charging of the rechargeable power source, determining a heat loss in the primary coil during charging of the rechargeable power source, determining an estimated power stored in the rechargeable power source by multiplying the charge current by the open-circuit voltage, subtracting the determined heat loss in the secondary coil and the estimated power stored from the power delivered to the primary coil, and adding the estimated energy absorbed by tissue of patient 12 to the power delivered to primary coil 48. Although FIG. 5 describes incorporating energy transferred to tissue from both resistive heat losses from power source 18 and energy directly absorbed by the tissue from the primary coil, only one of these energy sources may be considered in other examples.

In some examples, processor 50 may control energy generation by primary coil 48 for charging rechargeable power source 18 based on the estimated energy transfer to tissue of patient 12 (108). In some examples, processor 50 may control the energy generation of the external charging device by comparing the estimated energy transfer to an estimated energy transfer threshold, selecting a high power level for the primary coil of the external charging device when the estimated energy transfer has not exceeded the estimated heat transfer threshold, and selecting a low power level for the primary coil of the external device when the estimated energy transfer has exceeded the estimated energy transfer threshold.

Figure 6:
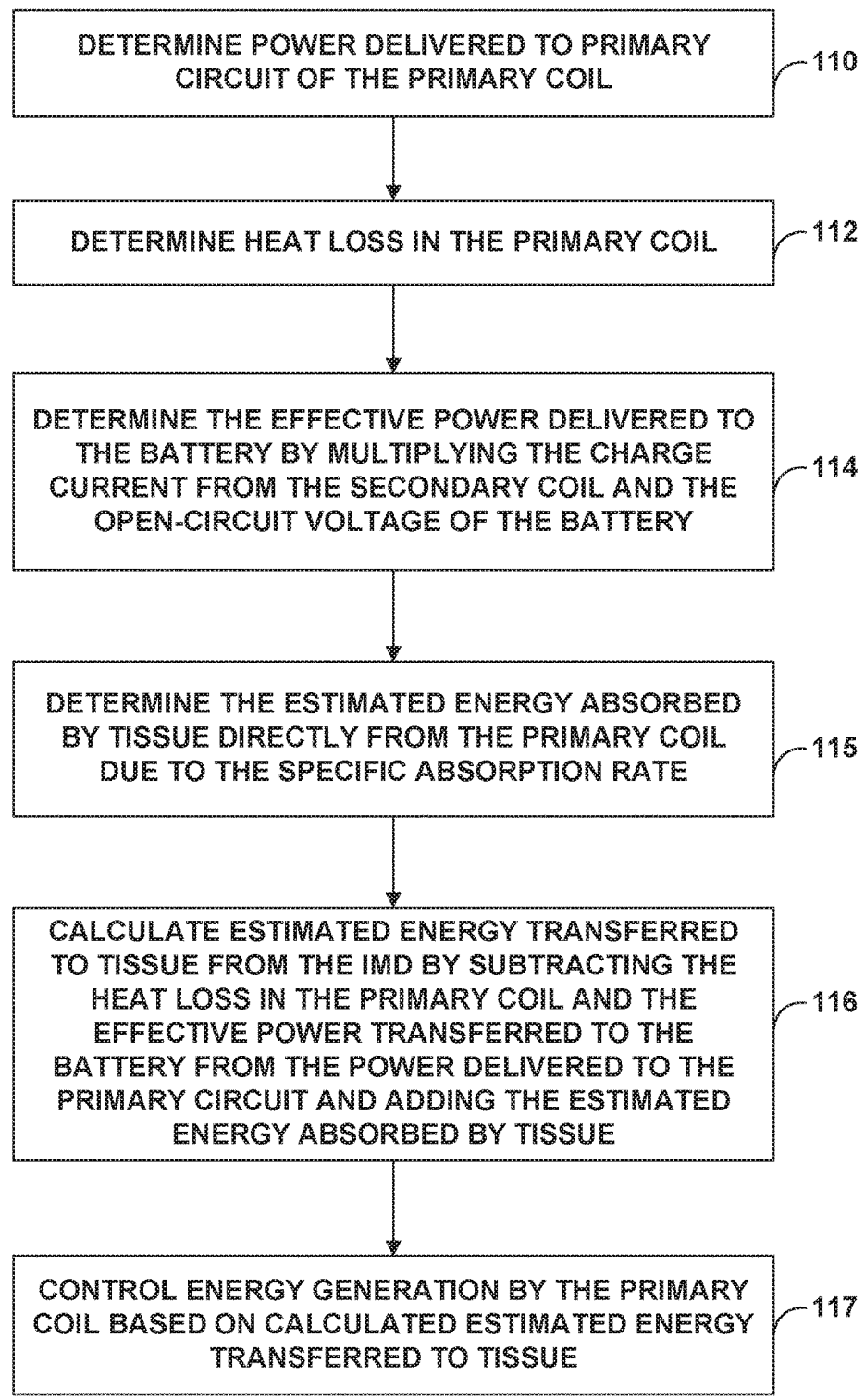
FIG. 6 is a flow diagram that illustrates an example technique for calculating an estimated energy transfer to tissue due to recharging and controlling energy generation by the external charging device based on the estimated energy transfer to tissue of a patient.

FIG. 6 is a flow diagram that illustrates an example technique for calculating an estimated energy transfer to tissue due to recharging and controlling energy generation by the external charging device based on the estimated energy transfer to tissue of a patient. Although processor 50 of charging device 20 will be described as generally performing the technique of FIG. 6, the technique of FIG. 6 may instead be performed by a combination of processors 30 and 50, in other examples.

As shown in FIG. 6, during a charging session for rechargeable power source 18, processor 50 may determine a power delivered to primary circuit of primary coil 48 (110). Processor 50 may also determine the heat loss in primary coil 48 (112). Processor 50 also determines the power stored in (i.e., the effective power delivered to) the battery (e.g., power source 18) by multiplying the charge current from the second coil and the open-circuit voltage of the battery (114). Additionally or alternatively, in some examples, processor 50 may determine an estimated energy absorbed by tissue of patient 12 from electromagnetic energy transmitted from the primary coil due to the specific absorption rate (115). Processor 50 may then calculate the estimated energy transfer to tissue of patient 12 from IMD 14 due to the recharging session of IMD 14 by subtracting the heat loss in the primary coil and the effective power transferred to the battery from the power delivered to the primary coil, and then add the estimated energy absorbed by tissue from the primary coil (116). Processor 50 may then control energy generation by primary coil 48 for charging rechargeable power source 18 based on the estimated energy transfer to tissue of patient 12 (117).

Figure 7:
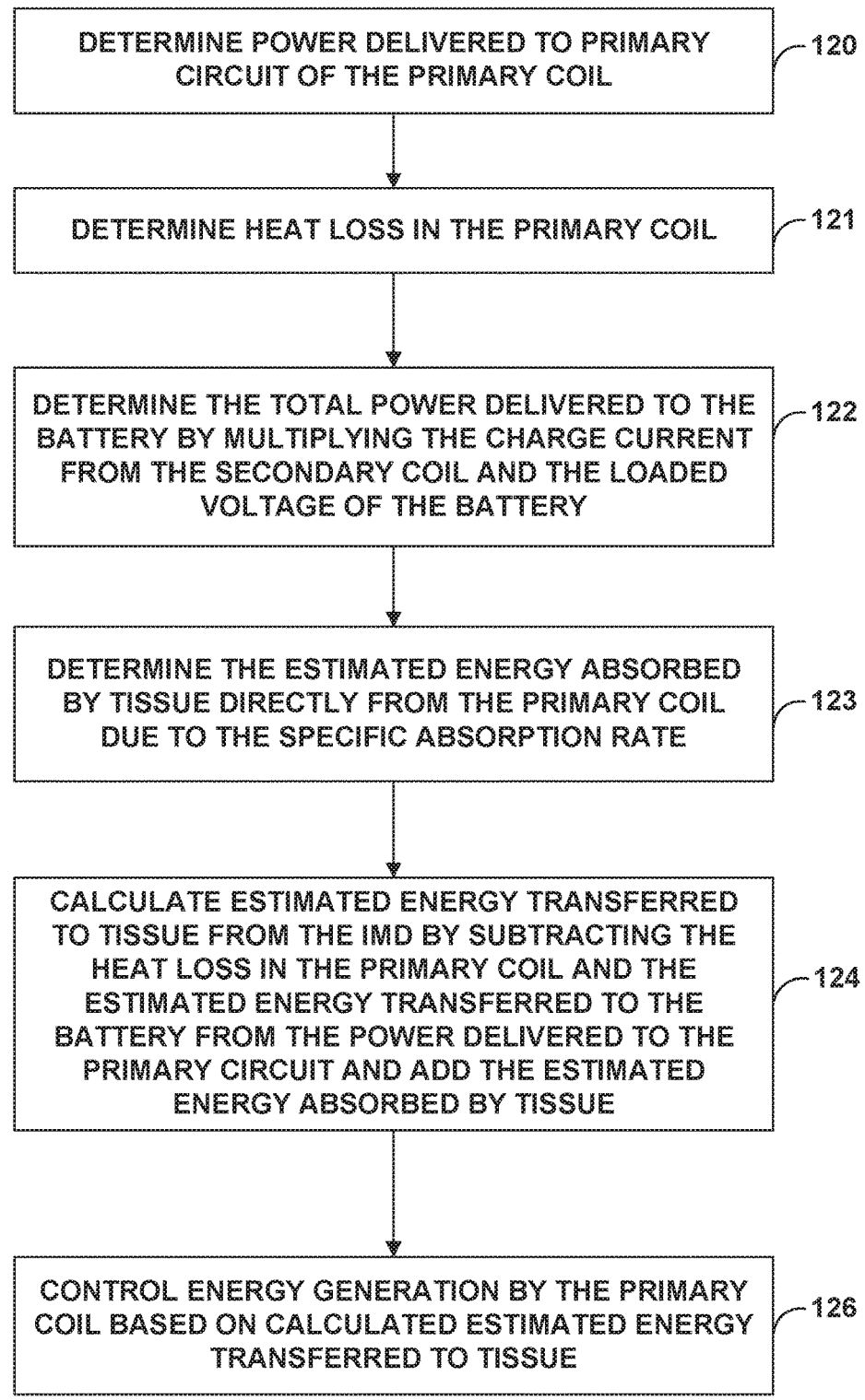
FIG. 7 is a flow diagram that illustrates another example technique for calculating an estimated energy transfer to tissue due to recharging and controlling energy generation by the external charging device based on the estimated energy transfer to tissue of a patient.

FIG. 7 is a flow diagram that illustrates another example technique for calculating an estimated energy transfer to tissue due to recharging and controlling energy generation by the external charging device based on the estimated energy transfer to tissue of a patient. Although processor 50 of charging device 20 will be described as generally performing the technique of FIG. 7, the technique of FIG. 7 may instead be performed by a combination of processors 30 and 50, in other examples.

As shown in FIG. 7, during a charging session for rechargeable power source 18, processor 50 may determine a power delivered to the primary circuit of primary coil 48 (120). Processor 50 may also determine the heat loss in primary coil 48 (121). Processor 50 may also determine the total power transferred to the battery by multiplying the charge current from the second coil and the loaded voltage of the battery (e.g., power source 18) (122). Processor 50 may then determine an estimated energy absorbed by tissue of patient 12 from electromagnetic energy transmitted from primary coil 48 due to the specific absorption rate (123). Using this information, processor 50 may calculate the estimated energy transfer to tissue of patient 12 from IMD 14 due to the recharging session of IMD 14 by subtracting the heat loss in primary coil 48 and the total power transferred to the battery from the power delivered to the primary circuit of primary coil 48 and then adding the estimated energy absorbed by tissue to the estimated energy transferred to tissue of patient 12 (124). In this manner, the estimated energy transfer to tissue calculated in step 124 may incorporate the energy directly absorbed by tissue from inductive coupling, but the calculation does not include resistive heat losses in power source 18 of IMD 14. This process may be appropriate when resistive heat losses are negligible, in some examples. When monitoring energy transfer, processor 50 may control energy generation by primary coil 48 for charging rechargeable power source 18 based on the estimated energy transfer to tissue of patient 12 (126).

Figure 8:
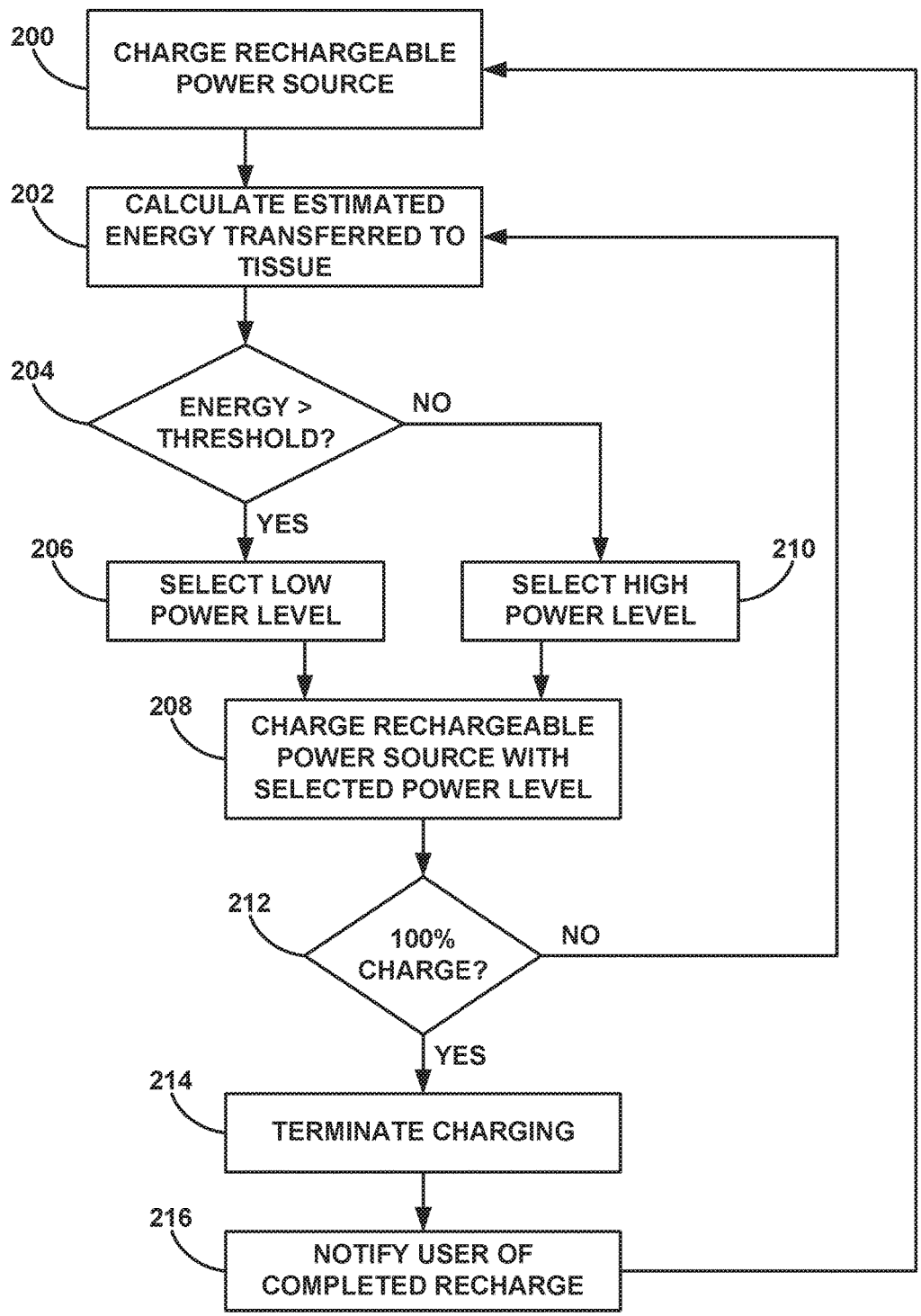
FIG. 8 is a flow diagram that illustrates an example technique for selecting a power level for charging an implantable rechargeable power source based on a calculated estimated energy transfer to tissue of a patient.

FIG. 8 is a flow diagram that illustrates an example technique for selecting a power level for charging an implantable rechargeable power source based on a calculated estimated energy transfer to tissue of patient 12. Although processor 50 of charging device 20 will be described as generally performing the technique of FIG. 8, the technique of FIG. 8 may instead be performed by a combination of processors 30 and 50, in other examples.

A charging session for rechargeable power source 18 may begin when processor 50 receives a charge request via user interface 54 (200). Processor 50 may calculate the estimated energy transferred to tissue of patient 12 (202). As described herein, in some examples, the estimated energy transfer may be calculated based on subtracting the heat loss of the primary coil and the effective power delivered to the battery from the power delivered to primary coil 48. As described herein, in some examples, the estimated energy transfer may be further calculated based on the addition of the resistive heat loss of the battery. As described herein, in some examples, the estimated energy transfer may be further calculated based on the addition of the energy absorbed by tissue of patient 12 from the power delivered to primary coil 48.

If the estimated energy transfer is less than the energy transfer threshold ("NO" branch of block 204), processor 50 selects the high power level for charging (210). If the estimated energy transfer is equal to or greater than the energy transfer threshold ("YES" branch of block 204), processor 50 selects the low power level for charging (206). If processor 50 is switching to a low power level from a high power level, user interface 54 may notify the user via a sound or visual indication that such change has occurred. Processor 50 then instructs charging module 58 to charge rechargeable power source 18 with the selected power level (208). In alternative examples, processor 30 may calculate the estimated energy transfer and or select the power level for charging. In these examples, processor 30 may incorporate the information received from IMD 14 to perform at least some of the elements of FIG. 8.

If rechargeable power source 18 has not yet reached a 100 percent, or full, charge level ("NO" branch of block 212), then processor 50 continues to calculate the estimated energy transfer to tissue (202). If rechargeable power source 18 has reached a 100 percent, or full, charge level ("YES" branch of block 212), then processor 50 may instruct charging module 58 to terminate charging (214). In other words, processor 50 may select a zero power level. Charging device 20 may subsequently notify the user of the completed recharge of rechargeable power source 18 and IMD 14 (216). This notification may be in the form of an audible alert or visual indicator provided by user interface 54. Processor 50 may also terminate charging upon request from the user.

In alternative examples, processor 50 may not charge rechargeable power source 18 when the estimated energy transfer meets or exceeds the energy transfer threshold. Therefore, not even a low power level would be selected. The ability to charge rechargeable power source 18 at any power level after the estimated energy transfer has exceeded the energy transfer threshold may be dependent upon how much heat is generated in IMD 14 when various power levels are used to charge rechargeable power source 18. Although a low power level may be acceptable for charging at any time in some systems and patients, other systems may be programmed to not allow any charging after the energy transfer threshold is exceeded.

This disclosure is primary directed to wireless transfer of energy between two coils (e.g., inductive coupling). However, one or more aspects of this disclosure may also be applicable to energy transfer involving a physical connection between a charging device and a rechargeable power supply. For example, aspects of this disclosure may be applicable to charging the power supply of an IMD by inserting a needle coupled to an external charging device through the skin and into a port of the IMD. Although physical connections for energy transfer may not introduce heat losses due to energy transfer between wireless coils, heat may still be generated and lost to the patient from components within the IMD (e.g., the resistive heat loss of the battery being charged and circuits involved in the recharging of the power supply).

Figure 9:
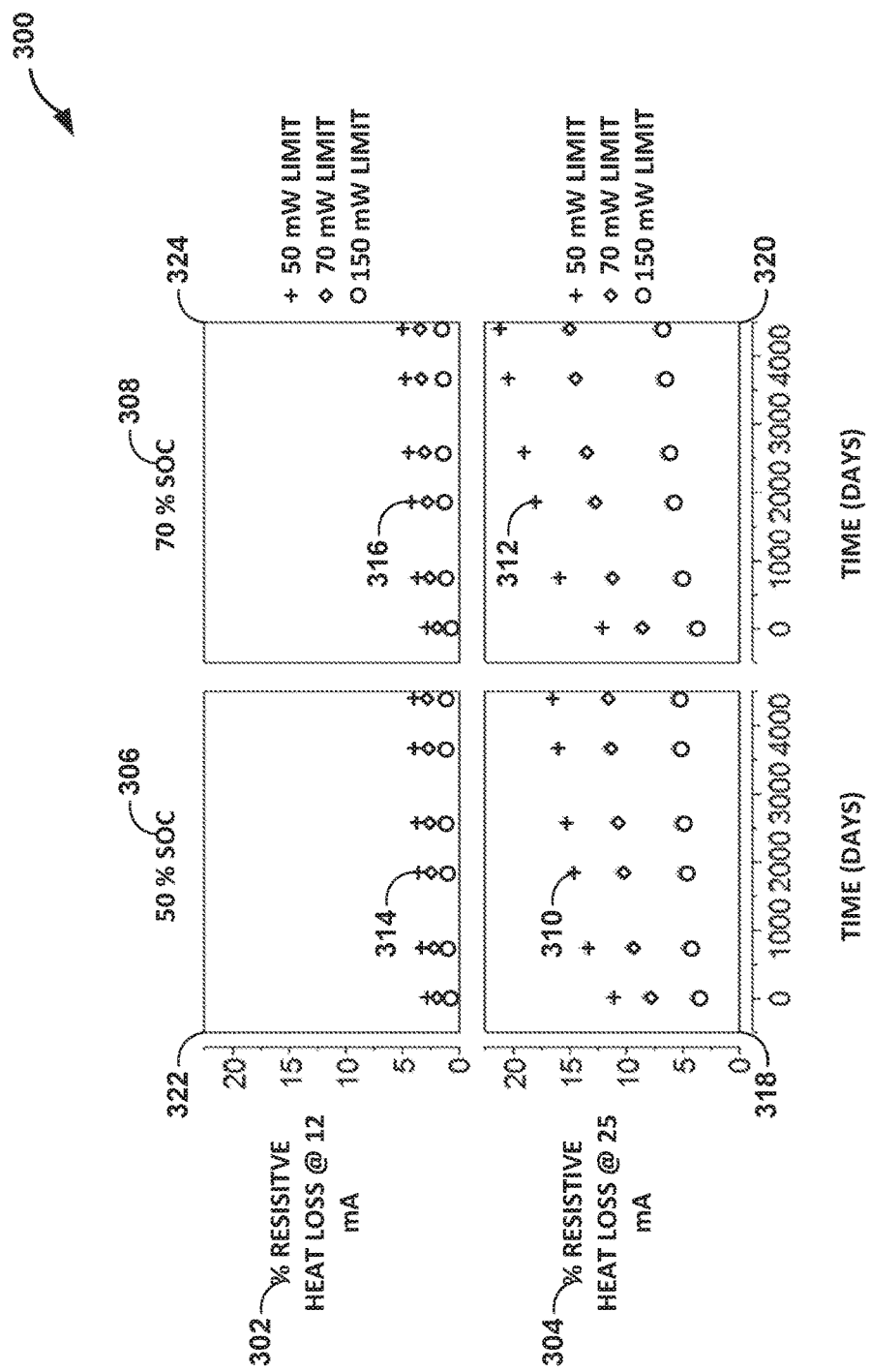
FIG. 9 is a chart that illustrates an example of resistive heat losses due to charge resistance of the rechargeable power source of the IMD as a percentage of the estimated energy transfer limit to tissue over time.

FIG. 9 is a chart that illustrates an example of resistive heat loss due to charge resistance of rechargeable power source 18 of IMD 14 as a percentage of the estimated energy transfer limit to tissue over time. Similar energy transfer limits may be used instead for instantaneous energy transfer as opposed to a cumulative energy transfer limit over a specific period of time. In the example of FIG. 9, chart 300 includes resistive heat loss 302 and 304, state-of-charge (SOC) 306 and 308, data points 310-316, and windows 318-324.

Resistive heat loss 302 may be the resistive heat loss as a percentage of an estimated energy transfer limit at twelve milliamps (mA) charge current. Resistive heat loss 304 may be the resistive heat loss as a percentage of estimated energy transfer limit at twenty-five mA charge current.

SOC 306 may be a percentage of the state of charge of a battery. In the example of FIG. 9, SOC 306 indicates a fifty percent stage of charge. SOC 308 may be another percentage of the state of charge of a battery. In the example of FIG. 9, SOC 308 indicates a seventy percent stage of charge.

Data points 310-316 each represent respective data of a battery with an age of two thousand days with a fifty milliwatt (mW) estimated energy transfer limit. Windows 318-322 each displays respective data points of a resistive heat loss of a battery as percentage over a period of time at different estimated energy transfer limits (e.g., 50 mW, 70 mW, and 150 mW).

In the example of FIG. 9, data point 310 indicates that a battery has a resistive heat loss 304 of approximately fifteen percent of the fifty mW estimated energy transfer limit at two-thousand days age, a twenty-five mA charge current, and at fifty percent SOC. Data point 312 indicates that a battery has a resistive heat loss 304 of eighteen percent the fifty mW estimated energy transfer limit at two-thousand days, twenty-five mA charge current, and at seventy percent SOC. Data point 314 indicates that a battery has a resistive heat loss 302 of four percent the fifty mW estimated energy transfer limit at two-thousand days, twelve mA charge current, and at fifty percent SOC. Data point 316 indicates that a battery has a resistive heat loss 302 of five percent the fifty mW estimated energy transfer limit at two-thousand days, twelve mA charge current, and at seventy percent SOC.

As illustrated in each of windows 318-324 of FIG. 9, the data points indicate a general upward trend of resistive heat losses 302 and 304 as a percentage of different estimated energy transfer limits over time. In the example of FIG. 9, window 320 illustrates a data point at day zero that indicates a battery has resistive heat loss 304 of twelve percent the fifty mW estimated energy transfer limit when the battery has a seventy percent SOC and twenty-five mA charge current. In the example of FIG. 9, window 320 illustrates a data point at greater than four thousand days that indicates a battery has resistive heat loss 304 of twenty-two percent the fifty mW estimated energy transfer limit when the battery has a seventy percent SOC and twenty-five mA charge current. In these examples, window 320 indicates a ten percent increase in resistive heat loss 304 over four thousand days.

In the example of FIG. 9, resistive heat losses 302 and 304 are each a function of SOC, time, and charge current. As each of the variables of SOC, time, and charge increase, resistive heat losses 302 and 304 also increase. Resistive heat losses 302 and 304 as illustrated in FIG. 9 may be interpreted as an amount of error between Equation 4 and Equation 1 as described in FIG. 4 because Equation 1 does not account for resistive heat losses 302 and 304. In some examples, charging device 20 and/or IMD 14 as described in FIGS. 2 and 3 may switch between using Equations 1 and 3 based on the amount of error of Equation 1. In some examples, charging device 20 and/or IMD 14 may use Equation 1 to calculate the estimated energy transfer to tissue of patient 12 when resistive heat loss 302 is below some threshold, such as two percent or some other negligible percentage. Conversely, charging device 20 and/or IMD 14 may use Equation 4 to calculate the estimated energy transfer to tissue of patient 12 when resistive heat loss 302 is above two percent for example. The threshold for determining whether resistive heat losses from power source 18 should be considered may be below two percent, such as 0.5 percent in some examples, or greater than two percent, such as five percent in other examples.

Although the example of FIG. 9 is primarily directed to resistive heat loss, one or more aspects of the example of FIG. 9 may also be applicable to energy absorbed by tissue of patient 12. For example, one or more aspects of the example of FIG. 9 for determining the amount of error of Equation 1 may also be applicable to determining the amount of error from the difference between Equation 1 and Equations 3, 4, 5, 6, or some combination therein. In another example, one or more aspects of the example of FIG. 9 for switching between Equation 1 and Equation 4 may also be applicable to switching between Equations 1, 3, 4, 5, 6, or some combination therein.

The following examples illustrate methods, devices, and systems described herein.

EXAMPLE 1 a method for controlling charging of a rechargeable power source of an implantable medical device in a patient, the method comprising: determining, by a processor, an estimated power stored in the rechargeable power source during charging of the rechargeable power source, the estimated power stored being separate from a resistive heat loss of the rechargeable power source during charging of the rechargeable power source; calculating, by the processor, an estimated energy transfer to tissue of the patient during charging of the rechargeable power source, the estimated energy transfer including the resistive heat loss of the rechargeable power source; and controlling, by the processor and based on the estimated energy transfer to the tissue, energy generation by a primary coil of an external charging device for charging the rechargeable power source via a secondary coil of the implantable medical device.

EXAMPLE 2 the method of example 1, wherein determining the estimated power stored in the rechargeable power source comprises: determining a charge current applied to the rechargeable power source; and determining an open-circuit voltage of the rechargeable power source, wherein the open-circuit voltage does not incorporate resistance of the rechargeable power source that results in the resistive heat loss when the charge current is applied to the rechargeable power source.

EXAMPLE 3

The method of any of examples 1 through 2, wherein determining the open-circuit voltage of the rechargeable power source comprises: determining a state of charge of the rechargeable power source; and determining the open-circuit voltage of the rechargeable power source based on the determined state of charge of the rechargeable power source.

EXAMPLE 4

The method of any of examples 1 through 3, wherein calculating the estimated energy transfer to tissue of the patient during charging of the rechargeable power source that includes the resistive heat loss from the rechargeable power source comprises: determining a power delivered to the primary coil during charging of the rechargeable power source; determining a heat loss in the primary coil during charging of the rechargeable power source; determining the estimated power stored in the rechargeable power source by multiplying the charge current by the open-circuit voltage; and subtracting the determined heat loss in the secondary coil and the estimated power stored in the rechargeable power source from the power delivered to the primary coil.

EXAMPLE 5

The method of any of examples 1 through 4, further comprising determining the resistive heat loss by: measuring a charge current applied to the rechargeable power source; measuring a loaded voltage across the rechargeable power source; determining an open-circuit voltage of the rechargeable power source; determining a voltage difference between the loaded voltage and the open-circuit voltage, wherein the voltage difference is due to a charge resistance of the rechargeable power source; and determining the resistive heat loss from the rechargeable power source by multiplying the charge current and the voltage different due to the charge resistance of the rechargeable power source.

EXAMPLE 6

The method of any of examples 1 through 5, further comprising: determining, by the processor, an estimated energy absorbed by tissue of the patient from electromagnetic energy transmitted from the primary coil during charging of the rechargeable power source, wherein calculating the estimated energy transfer to tissue comprises calculating the estimated energy transfer to tissue of the patient that includes the determined energy absorbed by tissue.

EXAMPLE 7

The method of example 6, wherein determining the estimated energy absorbed by tissue of the patient comprises: determining a current delivered to the primary coil; determining a frequency of the electromagnetic energy emitted by the primary coil; and determining, based on the current delivered to the primary coil and the frequency of the electromagnetic energy emitted by the primary coil, the estimated energy absorbed by tissue of the patient.

EXAMPLE 8

The method of any of examples 6 through 7, wherein determining the estimated energy absorbed by tissue of the patient comprises: determining a volume of tissue subjected to absorption of the electromagnetic energy emitted by the primary coil; and determining, based on the area of tissue, the estimated energy absorbed by tissue of the patient.

EXAMPLE 9

The method of any of examples 6 through 8, wherein calculating the estimated energy transfer to tissue of the patient during charging of the rechargeable power source that includes the resistive heat loss from the rechargeable power source comprises: determining a power delivered to the primary coil during charging of the rechargeable power source; determining a heat loss in the primary coil during charging of the rechargeable power source; determining the estimated power stored in the rechargeable power source by multiplying a charge current applied to the rechargeable power source by an open-circuit voltage of the rechargeable power source; subtracting the determined heat loss in the secondary coil and the estimated power stored in the rechargeable power source from the power delivered to the primary coil; and adding the estimated energy absorbed by tissue of the patient to the power delivered to the primary coil to calculate the estimated energy transfer to tissue.

EXAMPLE 10

The method of any of examples 6 through 9, wherein controlling the energy generation by the primary coil of the external charging device comprises: comparing the estimated energy transfer to an estimated energy transfer threshold; selecting a high power level for the primary coil of the external charging device when the estimated energy transfer has not exceeded the estimated heat transfer threshold; and selecting a low power level for the primary coil of the external device when the estimated energy transfer has exceeded the estimated energy transfer threshold.

EXAMPLE 11

The method of any of examples 6 through 10, wherein controlling the energy generation by the primary coil of the external charging device comprises: generating a first electrical current in a primary coil of a charging device based on the selected power level; and inducing an electrical current in an implanted secondary coil associated with the rechargeable power source.

EXAMPLE 12

A device configured to performing the method of any of examples 1-11.

EXAMPLE 13

A system configured to perform the method of any of examples 1-11.

EXAMPLE 14

The system of example 13, wherein the system comprises the implantable medical device.

EXAMPLE 15

A means for performing the method of any of examples 1-11.

EXAMPLE 16 a method for controlling charging of a rechargeable power source of an implantable medical device in a patient, the method comprising: determining, by a processor, an estimated power stored in the rechargeable power source during charging of the rechargeable power source, the estimated power stored being separate from a resistive heat loss of the rechargeable power source during charging of the rechargeable power source; calculating, by the processor, an estimated energy transfer to tissue of the patient during charging of the rechargeable power source, the estimated energy transfer including the resistive heat loss of the rechargeable power source; and controlling, by the processor and based on the estimated energy transfer to the tissue, energy generation by a primary coil of an external charging device for charging the rechargeable power source via a secondary coil of the implantable medical device.

EXAMPLE 17 the method of example 16, wherein determining the estimated power stored in the rechargeable power source comprises: determining a charge current applied to the rechargeable power source; and determining an open-circuit voltage of the rechargeable power source, wherein the open-circuit voltage does not incorporate resistance of the rechargeable power source that results in the resistive heat loss when the charge current is applied to the rechargeable power source.

EXAMPLE 18 the method according to any of examples 16-17, wherein determining the open-circuit voltage of the rechargeable power source comprises: determining a state of charge of the rechargeable power source; and determining the open-circuit voltage of the rechargeable power source based on the determined state of charge of the rechargeable power source.

EXAMPLE 19 the method according to any of examples 16-18, wherein calculating the estimated energy transfer to tissue of the patient during charging of the rechargeable power source that includes the resistive heat loss from the rechargeable power source comprises: determining a power delivered to the primary coil during charging of the rechargeable power source; determining a heat loss in the primary coil during charging of the rechargeable power source; determining the estimated power stored in the rechargeable power source by multiplying the charge current by the open-circuit voltage; and subtracting the determined heat loss in the secondary coil and the estimated power stored in the rechargeable power source from the power delivered to the primary coil.

EXAMPLE 20 the method according to any of examples 16-19, further comprising determining the resistive heat loss by: measuring a charge current applied to the rechargeable power source; measuring a loaded voltage across the rechargeable power source; determining an open-circuit voltage of the rechargeable power source; determining a voltage difference between the loaded voltage and the open-circuit voltage, wherein the voltage difference is due to a charge resistance of the rechargeable power source; and determining the resistive heat loss from the rechargeable power source by multiplying the charge current and the voltage different due to the charge resistance of the rechargeable power source.

EXAMPLE 21 the method according to any of examples 16-20, further comprising: determining, by the processor, an estimated energy absorbed by tissue of the patient from electromagnetic energy transmitted from the primary coil during charging of the rechargeable power source, wherein calculating the estimated energy transfer to tissue comprises calculating the estimated energy transfer to tissue of the patient that includes the determined energy absorbed by tissue.

EXAMPLE 22 the method according to any of examples 16-21, wherein determining the estimated energy absorbed by tissue of the patient comprises: determining a current delivered to the primary coil; determining a frequency of the electromagnetic energy emitted by the primary coil; and determining, based on the current delivered to the primary coil and the frequency of the electromagnetic energy emitted by the primary coil, the estimated energy absorbed by tissue of the patient.

EXAMPLE 23 the method according to any of examples 16-22, wherein determining the estimated energy absorbed by tissue of the patient comprises: determining a volume of tissue subjected to absorption of the electromagnetic energy emitted by the primary coil; and determining, based on the volume of tissue, the estimated energy absorbed by tissue of the patient.

EXAMPLE 24 the method according to any of examples 16-23, wherein calculating the estimated energy transfer to tissue of the patient during charging of the rechargeable power source that includes the resistive heat loss from the rechargeable power source comprises: determining a power delivered to the primary coil during charging of the rechargeable power source; determining a heat loss in the primary coil during charging of the rechargeable power source; determining the estimated power stored in the rechargeable power source by multiplying a charge current applied to the rechargeable power source by an open-circuit voltage of the rechargeable power source; subtracting the determined heat loss in the secondary coil and the estimated power stored in the rechargeable power source from the power delivered to the primary coil; and adding the estimated energy absorbed by tissue of the patient to the power delivered to the primary coil to calculate the estimated energy transfer to tissue.

EXAMPLE 25 the method according to any of examples 16-24, wherein controlling the energy generation by the primary coil of the external charging device comprises: comparing the estimated energy transfer to an estimated energy transfer threshold; selecting a high power level for the primary coil of the external charging device when the estimated energy transfer has not exceeded the estimated heat transfer threshold; and selecting a low power level for the primary coil of the external device when the estimated energy transfer has exceeded the estimated energy transfer threshold.

EXAMPLE 26 the method according to any of examples 16-25 wherein controlling the energy generation by the primary coil of the external charging device comprises: generating a first electrical current in a primary coil of a charging device based on the selected power level; and inducing an electrical current in an implanted secondary coil associated with the rechargeable power source.

EXAMPLE 27 the method according to any of examples 16-26, further comprising measuring tissue temperature adjacent to the rechargeable power source.

EXAMPLE 28 the method according to any of examples 16-27, wherein the processor is within one of the implantable medical device or an external charging device.

EXAMPLE 29 a device comprising: a processor configured to: determine an estimated power stored in a rechargeable power source of an implantable medical device in a patient during charging of the rechargeable power source, the estimated power stored being separate from a resistive heat loss of the rechargeable power source during charging of the rechargeable power source; calculate an estimated energy transfer to tissue of the patient during charging of the rechargeable power source, the estimated energy transfer including the resistive heat loss of the rechargeable power source; and control, based on the estimated energy transfer to the tissue, energy generation by a primary coil of an external charging device for charging the rechargeable power source via a secondary coil of the implantable medical device.

EXAMPLE 30 the device of example 29, wherein the processor is configured to determine the estimated power stored in the rechargeable power source comprises the processor configured to: determine a charge current applied to the rechargeable power source; and determine an open-circuit voltage of the rechargeable power source, wherein the open-circuit voltage does not incorporate resistance of the rechargeable power source that results in the resistive heat loss when the charge current is applied to the rechargeable power source.

EXAMPLE 31 the device according to any of examples 29-30, wherein the processor is configured to determine the open-circuit voltage of the rechargeable power source comprises the processor configured to: determine a state of charge of the rechargeable power source; and determine the open-circuit voltage of the rechargeable power source based on the determined state of charge of the rechargeable power source.

EXAMPLE 32 the device according to any of examples 29-31, wherein the processor is configured to calculate the estimated energy transfer to tissue of the patient during charging of the rechargeable power source that includes the resistive heat loss from the rechargeable power source comprises the processor configured to: determine a power delivered to the primary coil during charging of the rechargeable power source; determine a heat loss in the primary coil during charging of the rechargeable power source; determine the estimated power stored in the rechargeable power source by multiplying the charge current by the open-circuit voltage; and subtract the determined heat loss in the secondary coil and the estimated power stored in the rechargeable power source from the power delivered to the primary coil.

EXAMPLE 33 the device according to any of examples 29-32, wherein the processor is further configured to determine the resistive heat loss, and wherein the processor is configured to determine the resistive heat loss comprises the processor configured to: measure a charge current applied to the rechargeable power source; measure a loaded voltage across the rechargeable power source; determine an open-circuit voltage of the rechargeable power source; determine a voltage difference between the loaded voltage and the open-circuit voltage, wherein the voltage difference is due to a charge resistance of the rechargeable power source; and determine the resistive heat loss from the rechargeable power source by multiplying the charge current and the voltage different due to the charge resistance of the rechargeable power source.

EXAMPLE 34 the device according to any of examples 29-33, wherein the processor is further configured to determine an estimated energy absorbed by tissue of the patient from electromagnetic energy transmitted from the primary coil during charging of the rechargeable power source, and wherein the processor is configured to calculate the estimated energy transfer to tissue comprises calculating the estimated energy transfer to tissue of the patient that includes the determined energy absorbed by tissue.

EXAMPLE 35 the device according to any of examples 29-34, wherein the processor is configured to determine the estimated energy absorbed by tissue of the patient comprises the processor configured to: determine a current delivered to the primary coil; determine a frequency of the electromagnetic energy emitted by the primary coil; and determine, based on the current delivered to the primary coil and the frequency of the electromagnetic energy emitted by the primary coil, the estimated energy absorbed by tissue of the patient.

EXAMPLE 36 the device according to any of examples 29-35, wherein the processor is configured to determine the estimated energy absorbed by tissue of the patient comprises the processor configured to: determine a volume of tissue subjected to absorption of the electromagnetic energy emitted by the primary coil; and determine, based on the volume of tissue, the estimated energy absorbed by tissue of the patient.

EXAMPLE 37 the device according to any of examples 29-36, wherein the processor is configured to calculate the estimated energy transfer to tissue of the patient during charging of the rechargeable power source that includes the resistive heat loss from the rechargeable power source comprises the processor configured to: determine a power delivered to the primary coil during charging of the rechargeable power source; determine a heat loss in the primary coil during charging of the rechargeable power source; determine the estimated power stored in the rechargeable power source by multiplying a charge current applied to the rechargeable power source by an open-circuit voltage of the rechargeable power source; subtract the determined heat loss in the secondary coil and the estimated power stored in the rechargeable power source from the power delivered to the primary coil; and add the estimated energy absorbed by tissue of the patient to the power delivered to the primary coil to calculate the estimated energy transfer to tissue.

EXAMPLE 38 a system comprising: means for determining an estimated power stored in the rechargeable power source during charging of the rechargeable power source, the estimated power stored being separate from a resistive heat loss of the rechargeable power source during charging of the rechargeable power source; means for calculating an estimated energy transfer to tissue of the patient during charging of the rechargeable power source, the estimated energy transfer including the resistive heat loss of the rechargeable power source; and means for controlling, based on the estimated energy transfer to the tissue, energy generation by a primary coil of an external charging device for charging the rechargeable power source via a secondary coil of the implantable medical device.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory that is tangible. The computer-readable storage media may be referred to as non-transitory. A server, client computing device, or any other computing device may also contain a more portable removable memory type to enable easy data transfer or offline data analysis.

The techniques described in this disclosure, including those attributed to various processors or modules (e.g., processors 30 and 50) and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, remote servers, remote client devices, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an external or implantable device, an integrated circuit (IC) or a set of ICs, and/or discrete electrical circuitry, residing in an implantable device or system, for example.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media. The computer-readable storage medium may also be referred to as storage devices.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

What is claimed is:

1. A method for controlling charging of a rechargeable power source of an implantable medical device in a patient, the method comprising:
    determining, by processing circuitry, an estimated power stored in the rechargeable power source during charging of the rechargeable power source, the estimated power stored being separate from a resistive heat loss of the rechargeable power source during charging of the rechargeable power source;
    calculating, by the processing circuitry, an estimated energy transfer to tissue of the patient during charging of the rechargeable power source, the estimated energy transfer including the resistive heat loss of the rechargeable power source; and
    controlling, by the processing circuitry and based on the estimated energy transfer to the tissue, energy generation by a primary coil of an external charging device for charging the rechargeable power source via a secondary coil of the implantable medical device.

2. The method of claim 1, wherein determining the estimated power stored in the rechargeable power source comprises:
    determining a charge current applied to the rechargeable power source; and
    determining an open-circuit voltage of the rechargeable power source, wherein the open-circuit voltage does not incorporate resistance of the rechargeable power source that results in the resistive heat loss when the charge current is applied to the rechargeable power source.

3. The method of claim 2, wherein determining the open-circuit voltage of the rechargeable power source comprises:
determining a state of charge of the rechargeable power source; and
determining the open-circuit voltage of the rechargeable power source based on the determined state of charge of the rechargeable power source.

4. The method of claim 1, wherein calculating the estimated energy transfer to tissue of the patient during charging of the rechargeable power source that includes the resistive heat loss from the rechargeable power source comprises:
determining a power delivered to the primary coil during charging of the rechargeable power source;
determining a heat loss in the primary coil during charging of the rechargeable power source;
determining the estimated power stored in the rechargeable power source by multiplying the charge current by the open-circuit voltage; and
subtracting the determined heat loss in the secondary coil and the estimated power stored in the rechargeable power source from the power delivered to the primary coil.

5. The method of claim 1, further comprising determining the resistive heat loss by:
measuring a charge current applied to the rechargeable power source;
measuring a loaded voltage across the rechargeable power source;
determining an open-circuit voltage of the rechargeable power source;
determining a voltage difference between the loaded voltage and the open-circuit voltage, wherein the voltage difference is due to a charge resistance of the rechargeable power source; and
determining the resistive heat loss from the rechargeable power source by multiplying the charge current and the voltage different due to the charge resistance of the rechargeable power source.

6. The method of claim 1, further comprising:
determining, by the processing circuitry, an estimated energy absorbed by tissue of the patient from electromagnetic energy transmitted from the primary coil during charging of the rechargeable power source, wherein calculating the estimated energy transfer to tissue comprises calculating the estimated energy transfer to tissue of the patient that includes the determined energy absorbed by tissue.

7. The method of claim 6, wherein determining the estimated energy absorbed by tissue of the patient comprises:
determining a current delivered to the primary coil;
determining a frequency of the electromagnetic energy emitted by the primary coil; and
determining, based on the current delivered to the primary coil and the frequency of the electromagnetic energy emitted by the primary coil, the estimated energy absorbed by tissue of the patient.

8. The method of claim 6, wherein determining the estimated energy absorbed by tissue of the patient comprises:
determining a volume of tissue subjected to absorption of the electromagnetic energy emitted by the primary coil; and
determining, based on the area of tissue, the estimated energy absorbed by tissue of the patient.

9. The method of claim 6, wherein calculating the estimated energy transfer to tissue of the patient during charging of the rechargeable power source that includes the resistive heat loss from the rechargeable power source comprises:
determining a power delivered to the primary coil during charging of the rechargeable power source;
determining a heat loss in the primary coil during charging of the rechargeable power source;
determining the estimated power stored in the rechargeable power source by multiplying a charge current applied to the rechargeable power source by an open-circuit voltage of the rechargeable power source;
subtracting the determined heat loss in the secondary coil and the estimated power stored in the rechargeable power source from the power delivered to the primary coil; and
adding the estimated energy absorbed by tissue of the patient to the power delivered to the primary coil to calculate the estimated energy transfer to tissue.

10. The method of claim 1, wherein controlling the energy generation by the primary coil of the external charging device comprises:
comparing the estimated energy transfer to an estimated energy transfer threshold;
selecting a high power level for the primary coil of the external charging device when the estimated energy transfer has not exceeded the estimated heat transfer threshold; and
selecting a low power level for the primary coil of the external device when the estimated energy transfer has exceeded the estimated energy transfer threshold.

11. The method of claim 10, wherein controlling the energy generation by the primary coil of the external charging device comprises:
generating a first electrical current in a primary coil of the external charging device based on the selected power level; and
inducing an electrical current in an implanted secondary coil associated with the rechargeable power source.

12. A medical device for controlling delivery of electrical stimulation to a patient and comprising processing circuitry configured to control charging of a rechargeable power source of an implantable medical device in a patient by:
determining an estimated power stored in the rechargeable power source during charging of the rechargeable power source, the estimated power stored being separate from a resistive heat loss of the rechargeable power source during charging of the rechargeable power source;
calculating an estimated energy transfer to tissue of the patient during charging of the rechargeable power source, the estimated energy transfer including the resistive heat loss of the rechargeable power source; and
controlling, based on the estimated energy transfer to the tissue, energy generation by a primary coil of an external charging device for charging the rechargeable power source via a secondary coil of the implantable medical device.

13. The medical device of claim 12, wherein, to determine the estimated power stored in the rechargeable power source, the processing circuitry is further configured to:
determine a charge current applied to the rechargeable power source; and determine an open-circuit voltage of the rechargeable power source, wherein the open-circuit voltage does not incorporate resistance of the rechargeable power source that results in the resistive heat loss when the charge current is applied to the rechargeable power source.

14. The medical device of claim 13, wherein, to determine the open-circuit voltage of the rechargeable power source, the processing circuitry is further configured to:
determine a state of charge of the rechargeable power source; and
determine the open-circuit voltage of the rechargeable power source based on the determined state of charge of the rechargeable power source.

15. The medical device of claim 12, wherein, to calculate the estimated energy transfer to tissue of the patient during charging of the rechargeable power source that includes the resistive heat loss from the rechargeable power source, the processing circuitry is further configured to:
determine a power delivered to the primary coil during charging of the rechargeable power source;
determine a heat loss in the primary coil during charging of the rechargeable power source;
determine the estimated power stored in the rechargeable power source by multiplying the charge current by the open-circuit voltage; and
subtract the determined heat loss in the secondary coil and the estimated power stored in the rechargeable power source from the power delivered to the primary coil.

16. The medical device of claim 12, further comprising measurement circuitry configured to:
measure a charge current applied to the rechargeable power source; and
measure a loaded voltage across the rechargeable power source; and
wherein the processing circuitry is further configured to determine the resistive heat loss by:
determining an open-circuit voltage of the rechargeable power source;
determining a voltage difference between the loaded voltage and the open-circuit voltage, wherein the voltage difference is due to a charge resistance of the rechargeable power source; and
determining the resistive heat loss from the rechargeable power source by multiplying the charge current and the voltage different due to the charge resistance of the rechargeable power source.

17. The medical device of claim 12, wherein the processing circuitry is further configured to:
determine an estimated energy absorbed by tissue of the patient from electromagnetic energy transmitted from the primary coil during charging of the rechargeable power source, wherein, to calculate the estimated energy transfer to tissue, the processing circuitry is further configured to calculate the estimated energy transfer to tissue of the patient that includes the determined energy absorbed by tissue.

18. The medical device of claim 17, wherein, to determine the estimated energy absorbed by tissue of the patient, the processing circuitry is further configured to:
determine a current delivered to the primary coil;
determine a frequency of the electromagnetic energy emitted by the primary coil; and
determine, based on the current delivered to the primary coil and the frequency of the electromagnetic energy emitted by the primary coil, the estimated energy absorbed by tissue of the patient.

19. The medical device of claim 17, wherein, to determine the estimated energy absorbed by tissue of the patient, the processing circuitry is further configured to:
determine a volume of tissue subjected to absorption of the electromagnetic energy emitted by the primary coil; and
determine, based on the area of tissue, the estimated energy absorbed by tissue of the patient.

20. The medical device of claim 17, wherein, to calculate the estimated energy transfer to tissue of the patient during charging of the rechargeable power source that includes the resistive heat loss from the rechargeable power source, the processing circuitry is further configured to:
determine a power delivered to the primary coil during charging of the rechargeable power source;
determine a heat loss in the primary coil during charging of the rechargeable power source;
determine the estimated power stored in the rechargeable power source by multiplying a charge current applied to the rechargeable power source by an open-circuit voltage of the rechargeable power source;
subtract the determined heat loss in the secondary coil and the estimated power stored in the rechargeable power source from the power delivered to the primary coil; and
add the estimated energy absorbed by tissue of the patient to the power delivered to the primary coil to calculate the estimated energy transfer to tissue.

21. The medical device of claim 12, wherein, to control the energy generation by the primary coil of the external charging device, the processing circuitry is further configured to:
compare the estimated energy transfer to an estimated energy transfer threshold;
select a high power level for the primary coil of the external charging device when the estimated energy transfer has not exceeded the estimated heat transfer threshold; and
select a low power level for the primary coil of the external device when the estimated energy transfer has exceeded the estimated energy transfer threshold.

22. The medical device of claim 21, wherein, to control the energy generation by the primary coil of the external charging device, the processor is further configured to control the external charging device to:
generate a first electrical current in a primary coil of the external charging device based on the selected power level; and
induce an electrical current in an implanted secondary coil associated with the rechargeable power source.

23. A medical system for controlling charging of a rechargeable power source of an implantable medical device in a patient comprising:
means for determining an estimated power stored in the rechargeable power source during charging of the rechargeable power source, the estimated power stored being separate from a resistive heat loss of the rechargeable power source during charging of the rechargeable power source;
means for calculating an estimated energy transfer to tissue of the patient during charging of the rechargeable power source, the estimated energy transfer including the resistive heat loss of the rechargeable power source; and
means for controlling, based on the estimated energy transfer to the tissue, energy generation by a primary coil of an external charging device for charging the rechargeable power source via a secondary coil of the implantable medical device.

\* \* \* \* \*